(12) United States Patent
Steinman et al.

(10) Patent No.: US 8,257,700 B2
(45) Date of Patent: Sep. 4, 2012

(54) PROTEOMIC ANALYSIS OF ACTIVE MULTIPLE SCLEROSIS LESIONS

(75) Inventors: Lawrence M. Steinman, Stanford, CA (US); May H. Han, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 594 days.

(21) Appl. No.: 12/322,828

(22) Filed: Feb. 5, 2009

(65) Prior Publication Data

US 2009/0208481 A1 Aug. 20, 2009

Related U.S. Application Data

(60) Provisional application No. 61/063,805, filed on Feb. 5, 2008.

(51) Int. Cl.
*A61K 38/48* (2006.01)
(52) U.S. Cl. .................................. 424/94.64
(58) Field of Classification Search ............... 424/94.64
See application file for complete search history.

(56) References Cited

U.S. PATENT DOCUMENTS 7,074,402 B2 * 7/2006 Griffin et al. ............. 424/94.64
2007/0142272 A1 6/2007 Zlokovic et al.

OTHER PUBLICATIONS

Lucchinetti et al. Heterogeneity of Multiple Sclerosis Lesions:Implications for the Pathogenesis of Demyelination. Ann Neurol 2000;47:707-717.*
Demyelinating Diseases. Chapter 8, Clinical Neuropathology:text and color atlas. Edited by Catherine Haberland. p. 157-168. 2007.*
Beckmann; et al., "The structure and evolution of a 461 amino acid human protein C precursor and its messenger RNA, based upon the DNA sequence of cloned human liver cDNAs", Nucleic Acids Research (1985), 13 (14):5233-5247.
Bernard; et al., "Efficacy and Safety of Recombinant Human Activated Protein C for Severe Sepsis", The New England Journal of Medicine (2001), 344(10):699-709.
Foster; et al., "The nucleotide sequence of the gene for human protein C", PNAS (1985), 82:4673-4677.
Kuhlmann; et al., "Diagnosis of inflammatory demyelination in biopsy specimens: a practical approach", Acta Neuropathol (2008), 115:275-287.
Lassmann, "Addendum", Brain Pathol. (2007), 17(3):325.
Lassmann; et al., "Heterogeneity of multiple sclerosis pathogenesis: implications for diagnosis and therapy", Trends in Molecular Medicine (2001), 7(3):115-121.
Lock; et al., "Gene-microarray analysis of multiple sclerosis lesions yields new targets validated in autoimmune encephalomyelitis", Nature Medicine (2002), 8(5):500-508.
Lucchinetti; et al., "Evidence for Pathogenic Heterogeneity in Multiple Sclerosis", Annals of Neurology (2004), 56(2):308.
Mosnier; et al., "Activated protein C variants with normal cytoprotective but reduced anticoagulant activity", Blood (2004), 104(6):1740-1744.
Oberholzer; et al., "Plasma Cytokine Measurements Augment Prognostic Scores as Indicators of Outcome in Patients with Severe Sepsis", Shock (2005), 23(6):488-493.
Ousman; et al., "Protective and therapeutic role for alphaB-crystallin in autoimmune demyelination", Nature (2007), 448:474-9.
Soldan; et al., "Heterogeneity of Pathogenesis in Multiple Sclerosis: Implications for Promotion of Remyelination", The Journal of Infectious Diseases (2002), 186(Suppl 2):S248-53.
Soligo; et al., "The apoptogenic response of human myeloid leukaemia cell lines and of normal and malignant haematopoietic progenitor cells to the proteasome inhibitor PSI", British Journal of Haematology (2001), 113:126-135.
Tompkins; et al., "An array of possibilities for multiple sclerosis", Nature Medicine (2002), 8(5):451-453.
Tsutsui; et al., "Expression of Cadherin-Catenin Complexes in Human Leukemia Cell Lines", J. Biochem. (1996), 120:1034-1039.
Tajouri et al., "Quantitative and qualitative changes in gene expression patterns characterize the activity of plaques in multiple sclerosis", Molecular Brain Research (2003), 119:170-183.
"Xigris. Drotecogin alfa (activated)", Eli Lilly and Company, © 2001, PV 3420 AMP, 9 pages.

* cited by examiner

*Primary Examiner* — Taeyoon Kim
(74) *Attorney, Agent, or Firm* — Bozicevic, Field & Francis LLP; Pamela J. Sherwood

(57) ABSTRACT

The invention provides methods for treating demyelinating inflammatory diseases by administering to the subject an effective amount of an agent that provides activated protein C activity, where the dose is effective to reduce the adverse clinical indicia of the disease. In some embodiments, the patient being treating is of the chronic active plaque type.

4 Claims, 5 Drawing Sheets
(2 of 5 Drawing Sheet(s) Filed in Color)

PROTEOMIC ANALYSIS OF ACTIVE MULTIPLE SCLEROSIS LESIONS

BACKGROUND OF THE INVENTION

Multiple sclerosis (MS) is an inflammatory and degenerative disease of the central nervous system (CNS) with diverse clinical presentations and heterogeneous histopathological features. Understanding the neuropathology of MS is essential to develop improved therapies. MS lesions or "plaques" in the CNS white matter have distinct histological and immunocytological characteristics depending on disease activity. This heterogeneity implies that there are discrete molecular events at different pathogenetic stages of MS. Therefore, identification of targets specific to pathological types of MS lesions may have therapeutic benefits during different stages of disease.

For example, Lucchinetti et al. (2000) Annals of Neurology 47(6):707-717 determined four patterns of disease into which MS lesions fit. All had inflammatory infiltrates by T lymphocytes and macrophages in common but segregated on the basis of plaque geography, distribution of myelin protein loss, evidence of immunoglobulin and complement deposition, and oligodendrocyte death.

Although patterns of demyelination were heterogeneous between patients, multiple lesions within a patient all manifested the same phenotype, suggesting that lesion patterns are distinct mechanisms present in subgroups of MS patients. Understanding the pathogenetic mechanisms in demyelinating lesions has significant implications for developing and implementing appropriate therapies. In particular, understanding the relative loss or sparing of oligodendrocytes will determine what therapeutic strategies have potential efficacy in an individual MS patient.

In MS, myelin reactive T cells enter into the brain and spinal cord and mediate destruction of the myelin sheath surrounding neurons resulting in progressive motor dysfunction and eventual paralysis. Current treatment strategies include switching the pro-inflammatory Th1 T cell phenotype to an anti-inflammatory Th2 response, preventing encephalitogenic T cells from extravasating into the brain, inducing T cell tolerance, anergy or apoptosis, and repairing or replacing damaged CNS cells, such as neurons and oligodendrocytes.

Goals for therapy include shortening acute exacerbations, decreasing frequency of exacerbations, and relieving symptoms; maintaining the patient's ability to walk is particularly important. Acute exacerbations may be treated with brief courses of corticosteroids. However, although they may shorten acute attacks and perhaps slow progression, corticosteroids have not been shown to affect long-term outcome.

Immunomodulatory therapy decreases frequency of acute exacerbations and delays eventual disability. Immunomodulatory drugs include interferons (IFNs), such as IFN-β1b and IFN-β1a. Glatiramer acetate may also be used. Other potential therapies include the immunosuppressant methotrexate and Natalizumab, an anti-$\alpha_4$ integrin antibody that inhibits passage of leukocytes across the blood-brain barrier. Immunosuppressants such as mycophenolate and cyclophosphamide have been used for more severe, progressive MS but are controversial.

In addition to suppressing the pathological immune response it is important to protect CNS cells from further damage and to induce repair of injured cells since some cells such as neurons have few progenitors in the adult mammalian brain and are thus limiting.

Limited therapeutic benefit achieved with the above-mentioned immunotherapies may relate to the apparent pathogenetic and clinical heterogeneity of MS. An improved understanding of the pathologic processes involved may allow therapies to be targeted to subgroups of MS patients that are most likely to respond. Clearly, in order to tailor therapy for each patient, classification of pathogenetic mechanism, preferably by using noninvasive methods, will be necessary.

In recent years, a "systems biology" approach using large-scale analysis of proteins and gene transcripts has illuminated new aspects of pathogenesis for complex disease networks including malignancies, neurodegenerative disorders and infections. Similarly, large-scale transcriptional profiling of MS lesions has identified involvement of novel molecules and pathways such as osteopontin and Notch/Jagged signalling, respectively. However, transcriptomic analysis fails to provide a comprehensive understanding of effector molecules involved in MS pathogenesis due to the susceptibility of mRNA to degradation and the discrepancy between mRNA and protein expression levels. Transcriptomic analysis also overlooks signaling molecules from serum, hormones and neurotransmitters.

The present invention provides an alternative approach, where characterization of MS lesions utilized focused proteomic analysis, enriched by laser-capture microdissection (LCM) and analyzed by sensitive tools such as mass spectrometry, provides functional insights into MS pathogenesis.

SUMMARY OF THE INVENTION

The invention provides methods for treating neurological inflammatory diseases, which may be demyelinating autoimmune diseases, such as multiple sclerosis, etc. It is shown herein that MS lesions are associated with the presence of proteins specific to that lesion type, and that reversing the physiological effects of these proteins can ameliorate disease. Proteins of interest include the proteins set forth in any one of Table 3, 4 and 5. In some embodiments the targeted protein is protein C inhibitor. In other embodiments the targeted protein is tissue factor.

In some embodiments of the invention, the neurological inflammatory disease is multiple sclerosis, which may be of the chronic active plaque (CAP) type. In one aspect, the invention is directed to a method to ameliorate the clinical effects of disease in a patient having one or more CAP-type lesions, comprising the steps of administering an agent that reverses the physiological effects of protein C inhibitor in a dose effective to reduce the severity of the disease. In some embodiments the agent is activated protein C (aPC), which is a well-defined anti-coagulant enzyme. The enzyme may be recombinantly produced human aPC. The enzyme may also be a variant aPC with reduced anticoagulant activity.

In certain embodiments, the methods of the invention comprise identifying the presence of one or more CAP-type lesions in the patient, administering to the patient an agent that reverses the physiological effects of protein C inhibitor in a dose effective to reduce the severity of the disease. The administering may be systemic or local administration that provides for a prolonged localized concentration, which may utilize sustained release implants, viscous solutions, or other topical formulation, are of particular interest.

In other embodiments, methods are provided for proteomic analysis of MS lesions, the method comprising staining a section of tissue suspected of containing one or more MS lesions, isolating lesions by laser microscopy, and performing sequencing of proteins present in the lesions by mass spectroscopy.

As provided herein, MS lesions were stained and classified by histological types: acute plaque (AP), chronic active plaque (CAP), and chronic plaque (CP). The lesions were isolated by LCM and saturated sequencing performed by mass spectrometry. The polypeptides thus identified can be analyzed by various means for specificity, utility as a therapeutic and/or diagnostic target, and the like. The markers are useful in screening, diagnostic and therapeutic applications.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
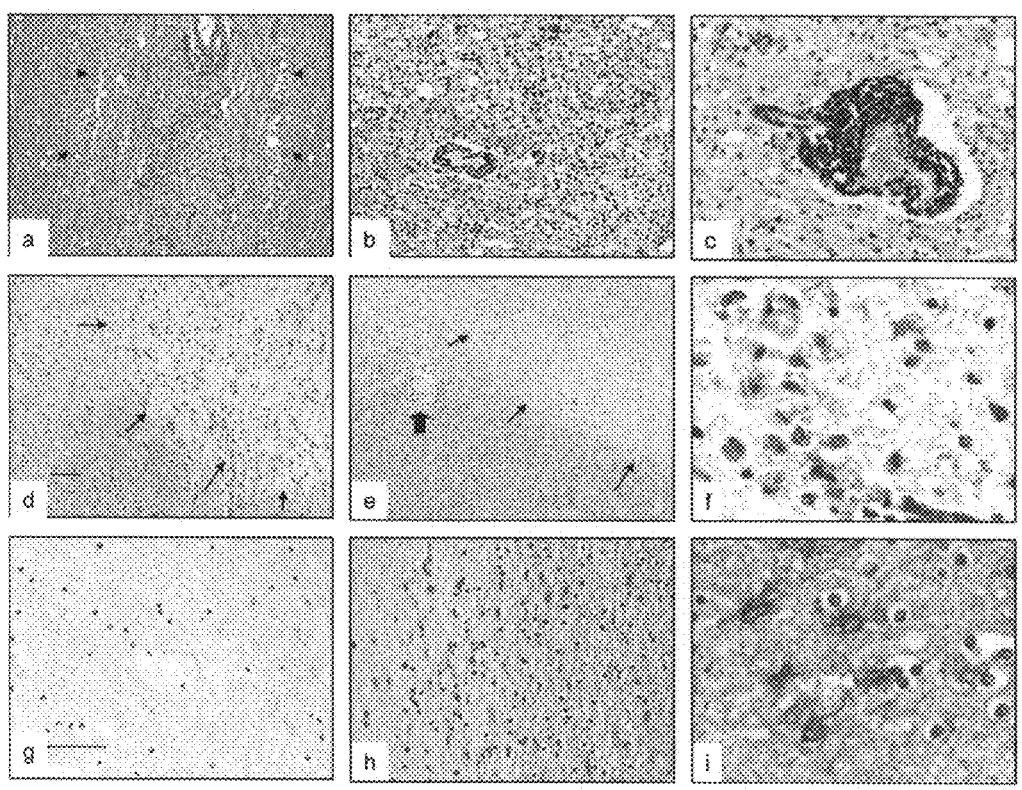
FIG. 1: Histopathology of MS brain lesions. (a,d,g=H&E; e,h=LFB; b,c,f,i=IH). a, b, c) Active plaque (AP). a) Marked inflammation, vacuolation (arrowheads) and edema. b) Patchy demyelination (normal myelin=brown), anti-$PLP_{200-219}$. c) Perivenous and parenchymal (arrows) inflammatory cells; anti-CD45. d, e, f Chronic active plaque (CAP). d, e) Well-demarcated lesion edge (arrows) with recent inflammation (e) (blocked arrow). f) Macrophages, on-going demyelination in CAP; anti-CD68. g, h, i) Chronic plaque (CP). g) Hypocellular fibrotic CP. h) Well-demarcated edge. i) Astrogliosis, anti-GFAP. Scale bars; d (a,d,e,f=50 µM, =25 µM (c,f,i), g (b,g,h)=50 µM.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

DEFINITIONS

"Diagnosis" as used herein generally includes determination of a subject's susceptibility to a disease or disorder, determination as to whether a subject is presently affected by a disease or disorder, prognosis of a subject affected by a disease or disorder (e.g., identification of disease states, stages of MS, or responsiveness of MS to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood, cerebral spinal fluid, and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

"Comparable cell" shall mean a cell whose type is identical to that of another cell to which it is compared. Examples of comparable cells are cells from the same cell line.

"Inhibiting" the onset of a disorder shall mean either lessening the likelihood of the disorder's onset, or preventing the onset of the disorder entirely. In the preferred embodiment, inhibiting the onset of a disorder means preventing its onset entirely. As used herein, onset may refer to a relapse in a patient that has ongoing relapsing remitting disease. The methods of the invention are specifically applied to patients that have been diagnosed with an autoimmune disease. Treatment is aimed at the treatment or prevention of relapses, which are an exacerbation of a pre-existing condition.

"Inhibiting" the expression of a gene in a cell shall mean either lessening the degree to which the gene is expressed, or preventing such expression entirely.

"Specifically hybridize" to a nucleic acid shall mean, with respect to a first nucleic acid, that the first nucleic acid hybridizes to a second nucleic acid with greater affinity than to any other nucleic acid.

"Specifically inhibit" the expression of a protein shall mean to inhibit that protein's expression (a) more than the expression of any other protein, or (b) more than the expression of all but 10 or fewer other proteins.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

The term "inflammatory" response is the development of a humoral (antibody mediated) and/or a cellular (mediated by antigen-specific T cells or their secretion products) response.

An "immunogen" is capable of inducing an immunological response against itself on administration to a mammal or due to autoimmune disease.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The subject methods are used for prophylactic or therapeutic purposes. As used herein, the term "treating" is used to refer to both prevention of relapses, and treatment of pre-existing conditions. For example, the prevention of autoimmune disease may be accomplished by administration of the agent prior to development of a relapse. The treatment of ongoing disease, where the treatment stabilizes or improves the clinical symptoms of the patient, is of particular interest.

Methods of the Invention

The invention provides methods for treating neurological inflammatory diseases, which may be a demyelinating autoimmune disease, such as multiple sclerosis. The methods of the invention comprise administering to the subject an effective amount of an agent that reverses the physiological effects of proteins demonstrated herein to be specifically associated with neurological lesions. Proteins of interest include the proteins set forth in any one of Table 3, 4 and 5. Of particular interest is the administration of an agent that provides protein C activity, particularly the administration of activated protein C (aPC), in a dose effective to decrease the severity of ongoing disease, where the aPC may be recombinantly produced human aPC; variant human aPC with reduced anticoagulant activity; and the like.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The delivery systems employ a number of routinely used pharmaceutical carriers.

Inflammatory neurological diseases include multiple sclerosis (MS), which is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive (primary progressive MS, PPMS). Relapsing remitting MS (RR MS) is characterized clinically by relapses and remissions that occur over months to years, with partial or full recovery of neurological deficits between attacks. Such patients manifest approximately 1 attack, or relapse, per year. Over 10 to 20 years, approximately 50% of RR MS patients develop secondary progressive MS (SP MS) which is characterized by incomplete recovery between attacks and accumulation of neurologic deficits resulting in increasing disability.

Diagnosis is indirect, by deduction from clinical, radiographic (brain plaques on magnetic resonance [MR] scan), and to a lesser extent laboratory (oligoclonal bands on CSF analysis) features. Typical cases can usually be diagnosed confidently on clinical grounds. The diagnosis can be suspected after a first attack. Later, a history of remissions and exacerbations and clinical evidence of CNS lesions disseminated in more than one area are highly suggestive.

MRI, the most sensitive diagnostic imaging technique, may show plaques. It may also detect treatable nondemyelinating lesions at the junction of the spinal cord and medulla (e.g., subarachnoid cyst, foramen magnum tumors) that occasionally cause a variable and fluctuating spectrum of motor and sensory symptoms, mimicking MS. Gadolinium-contrast enhancement can distinguish areas of active inflammation from older brain plaques. MS lesions may also be visible on contrast-enhanced CT scans; sensitivity may be increased by giving twice the iodine dose and delaying scanning (double-dose delayed CT scan).

Conventional treatments for MS include interferon β (Avonex, Betaseron, Rebif), Copaxone (Glatiramer acetate), and anti-VLA4 (Tysabri, natalizumab), any of which may be combined with the agents utilized in the present invention. MS is also treated with immunosuppressive agents including methylprednisolone, other steroids, methotrexate, cladribine and cyclophosphamide. Many biological agents, such as anti-IFNγ antibody, CTLA4-Ig (Abetacept), anti-CD20 (Rituxan), and other anti-cytokine agents are in clinical development for MS.

In some embodiments of the invention, a tissue section suspected of comprising a lesion is characterized by staining, e.g. with Hematoxylin and Eosin (H&E), Luxol Fast Blue (LFB), etc. Alternatively plaques may be characterized according to expression of the markers as described herein. The treatment with an agent may be selected on the basis of the lesion characterization. For example, a patient with a CAP type lesion may be selected for treatment with aPC.

Lesions can be characterized as acute plaque (AP) having florid parenchymal and perivascular inflammatory cell infiltration, abundant astroglial hypertrophy, myelin fragmentation, edema and ongoing demyelination with indistinct margins. CAP lesions have chronic demyelination, sharply defined margins and recent areas of inflammatory demyelination at the edges including pronounced immunoglobulin and complement reactivity associated with degenerating myelin at the active plaque edge and with myelin degradation products within macrophages. CP lesions have areas of demyelination with well-demarcated borders and abundant astrogliosis but few or no inflammatory cells. These latter two types of lesions show sharply demarcated perivenular demyelination with loss of all myelin proteins apparently occurring simultaneously. Sparing of oligodendrocytes in active plaques and repopulation of inactive plaques with high numbers of oligodendrocytes was observed.

A more complete description of the plaques is publicly available, for example as described, inter alia, by Kuhlmann et al. (2008) Acta Neuropathol.; Lassmann et al. (2007) Brain Pathol. 17(3):325; Lassmann et al. (2004) Ann Neurol. 56(2): 308; Lassmann et al. (2001) Trends Mol Med 7:115-2; each of which are specifically incorporated by references for teachings related to plaque classification.

The present invention identifies polypeptides that are differentially expressed in MS plaques. Methods are provided in which these polypeptides, which may be collectively referred to as plaque-specific markers, are used for assessing and treating disease. Methods may use one or a combination of markers, where a combination may include 2, 3 or more markers.

In some embodiments, the markers are expressed as a level at least 2× the expression level of a cell free of disease, e.g. a human oligodendrocyte or neural cell, or a differently classified plaque, where expression may be determined as the level of transcription, mRNA accumulation, and/or protein accumulation. In other embodiments the markers are expressed as a level at least 3×, at least 4×, at least 5×, at least 10×, at least 20× or greater, than the expression level of a counterpart non-diseased cell.

The present invention provides methods of using the markers described herein in diagnosis of MS, classification and treatment of MS and related conditions according to expression profiles. The methods are useful for characterizing plaques, facilitating diagnosis of MS and the severity and nature of the disease in a subject, facilitating a determination of the prognosis of a subject, and assessing the responsiveness of the subject to therapy. The detection methods of the invention can be conducted in vitro or in vivo, on isolated cells, or in whole tissues, e.g. needle biopsy samples, and the like.

A polynucleotide or polypeptide sequence that corresponds to, or represents a marker means that at least a portion of a sequence of the polynucleotide or polypeptide is present. A sequence may also be "identified" by a polynucleotide or polypeptide if the polynucleotide or polypeptide corresponds to or represents the marker. An "identifying sequence" is a minimal fragment of a sequence of contiguous nucleotides or amino acids that uniquely identifies or defines a polynucleotide or polypeptide sequence. Sequences of interest include those set forth in Tables 3-5, which are differentially expressed in the specified MS plaques.

Methods are also provided for optimizing therapy, by first classification, and based on that information, selecting the appropriate therapy, dose, treatment modality, etc. which optimizes the differential between delivery of a treatment to the undesirable target cells, while minimizing undesirable toxicity. The treatment is optimized by selection for a treatment that minimizes undesirable toxicity, while providing for effective anti-proliferative activity.

Therapeutic Agents

In one embodiment of the invention, agents that provide activated protein c activity, e.g. aPC polypeptides, nucleic acids encoding aPC, and the like are used in the treatment of inflammatory disease, including demyelinating autoimmune disease, such as MS.

"Activated protein C" shall mean the activated form of the human protein encoded by the mRNA sequence set forth in GenBank Accession No. NM_000312 and as described by Beckmann et al. (1985) Nucleic Acids Res. 13 (14), 5233-5247; and Foster et al. (1985) Proc. Nati. Acad. Sci. U.S.A. 82 (14), 46734677, all biologically active variants and homologues thereof. Protein C is a vitamin K-dependent serine protease zymogen. Purified human activated protein C selectively destroys factors Va and VIII:C in human plasma and thus has an important anticoagulant role. The protein is activated by thrombin.

An FDA approved recombinantly produced form of activated protein C is available as Drotrecogin alpha (activated), from Eli Lilly under the trade name XIGRIS. Drotrecogin alfa (activated) is a glycoprotein of approximately 55 kilodalton molecular weight, consisting of a heavy chain and a light chain linked by a disulfide bond. Drotrecogin alfa (activated) and human plasma-derived Activated Protein C have the same sites of glycosylation, although some differences in the glycosylation structures exist.

Variants of protein C have been described, e.g. see Mosnier et al. (2004) Blood 104:1740; Griffin et al. (2007) J Thromb Haemost. 2007 July; 5 Suppl 1:73-80; Preston et al. (2006) J Biol Chem. 281(39):28850-7; Gale et al. (2006) J Thromb Haemost. 4(6):1315-22; and Preston et al. (2005) FEBS J. 272(1):97-108; each of which is herein specifically incorporated by reference for teachings of protein C variants and their use.

Activated protein c polypeptides, which can be used in the methods of the invention, comprise at least about 50 amino acids, usually at least about 100 amino acids, at least about 150 amino acids, at least about 160 amino acids, at least about 170 amino acids, and which may include up to 175 amino acids of an activated protein c protein, or modifications thereof, and may further include fusion polypeptides as known in the art in addition to the provided sequences. The activated protein c sequence may be from any mammalian or avian species, e.g. primate sp., particularly humans; rodents, including mice, rats and hamsters; rabbits; equines, bovines, canines, felines; etc. Of particular interest are the human proteins.

In some embodiments of the invention, the aPC protein, or a functional fragment or variant thereof is administered to a patient. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

The sequence of activated protein c peptides as described above may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:3541 (1993); Sayers et al., Biotechniques 13:592-6 (1992); Jones and Winistorfer, Biotechniques 12:528-30 (1992); Barton et al., Nucleic Acids Res 18:7349-55 (1990); Marofti and Tomich, Gene Anal Tech 6:67-70 (1989); and Zhu Anal Biochem 177:1204 (1989).

The activated protein c for use in the subject methods may be produced from eukaryotic or prokaryotic cells, or may be synthesized in vitro. Where the protein is produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The aPC polypeptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Active polypeptides or polynucleotides can serve as the active ingredient in pharmaceutical compositions formulated for the treatment of various disorders as described above. The active ingredient is present in a therapeutically effective amount, i.e., an amount sufficient when administered to substantially modulate the effect of the targeted protein or polypeptide to treat a disease or medical condition mediated thereby. The compositions can also include various other agents to enhance delivery and efficacy, e.g. to enhance delivery and stability of the active ingredients.

Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The aPC compositions may be administered in a single dose, or in multiple doses, usually multiple doses over a period of time, e.g. daily, every-other day, weekly, semi-weekly, monthly etc. for a period of time sufficient to reduce severity of the disease, which may comprise 1, 2, 3, 4, 6, 10, or more doses.

Determining a therapeutically or prophylactically effective amount an agent that provides aPC activity can be done based on animal data using routine computational methods. In one embodiment, the therapeutically or prophylactically effective amount contains between about 0.1 mg and about 1 g of protein. In another embodiment, the effective amount contains between about 1 mg and about 100 mg of protein, as applicable. The effective dose will depend at least in part on the route of administration. The agents may be administered orally, in an aerosol spray; by injection, e.g. i.m., s.c., i.p., i.v., etc. The dose may be from about 0.1 µg/kg patient weight; about 1 µg/kg; about 10 µg/kg; to about 100 µg/kg.

Treating, treatment, or therapy of a disease or disorder shall mean lessening the severity of adverse clinical symptoms by administration of an aPC composition. As used herein, ameliorating a disease and treating a disease are equivalent.

The method also provide for combination therapy, where the combination may provide for additive or synergistic benefits. Combinations of activated protein c may be obtained with a second agent selected from one or more of the general classes of drugs commonly used in the non-antigen specific treatment of autoimmune disease, which include corticosteroids and disease modifying drugs; or from an antigen-specific agent. Corticosteroids have a short onset of action, but many disease modifying drugs take several weeks or months to demonstrate a clinical effect. These agents include methotrexate, leflunomide (Arava™), etanercept (Enbrel™), infliximab (Remicade™), adalimumab (Humira™), anakinra (Kineret™), rituximab (Rituxan™), CTLA4-Ig (abatacept), antimalarials, gold salts, sulfasalazine, d-penicillamine, cyclosporin A, cyclophosphamide azathioprine; and the like.

Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

Disease modifying anti-rheumatoid drugs, or DMARDs have been shown to alter the disease course and improve radiographic outcomes in RA. It will be understood by those of skill in the art that these drugs are also used in the treatment of other autoimmune diseases.

Methotrexate (MTX) is a frequent first-line agent because of its early onset of action (4-6 weeks), good efficacy, favorable toxicity profile, ease of administration, and low cost. MTX is the only conventional DMARD agent in which the majority of patients continue on therapy after 5 years. MTX is effective in reducing the signs and symptoms of RA, as well as slowing or halting radiographic damage. Although the immunosuppressive and cytotoxic effects of MTX are in part due to the inhibition of dihydrofolate reductase, the anti-inflammatory effects in rheumatoid arthritis appear to be related at least in part to interruption of adenosine and TNF pathways. The onset of action is 4 to 6 weeks, with 70% of patients having some response. A trial of 3 to 6 months is suggested.

Antigen specific therapeutic methods include administration of an antigen or epitope specific therapeutic agent. One method to induce immune tolerance is tolerizing DNA vaccines (Garren et al. (2001) Immunity, 15:15-22; Robinson et al. (2003) Nature Biotechnology 21:1033-9). Tolerizing DNA vaccines are DNA plasmids containing the regulatory regions necessary for expression of the encoded cDNA in mammalian cells, and would be engineered to contain cDNA sequence encoding all or a portion of activated protein c in order to induce immune tolerance to the encoded epitopes. To enhance the ability of such plasmids to induce immune tolerance, the immunostimulatory CpG sequences (Krieg et al. (1998) Trends Microbiol. 6:23-27) can be reduced in number or completely removed from the plasmid vector. Additionally, immunoinhibitory GpG sequences can be added to the vector (see Ho et al. (2005) J. Immunology, 175:6226-34).

As an alternative, or in addition to DNA tolerization, specific peptides, altered peptides, or proteins may be administered therapeutically to induce antigen-specific tolerance to treat autoimmunity. Native peptides targeted by the autoimmune response can be delivered to induce antigen-specific tolerance (Science 258:1491-4). Native peptides have been delivered intravenously to induce immune tolerance (J Neurol Sci. 152:31-8). Delivery of peptides that are altered from the native peptide, is also known in the art. Alteration of native peptides with selective changes of crucial residues (altered peptide ligands or "APL") can induce unresponsiveness or change the responsiveness of antigen-specific autoreactive T cells. In another embodiment, whole protein antigens targeted by the autoimmune response can be delivered to restore immune tolerance to treat autoimmunity (Science 263:1139).

Lesion Specific Markers

The invention provides polypeptides and polynucleotides that encode them that represent proteins that are differentially present in specific classes of MS lesions. These polynucleotides, polypeptides and fragments thereof have uses that include, but are not limited to, diagnostic probes, and primers as starting materials for probes and primers, as immunogens for antibodies useful in MS diagnosis and therapy, and the like as discussed herein.

In general, the term "polypeptide" as used herein refers to both the full length polypeptide, as well as portions or fragments thereof. "Polypeptides" also includes variants of the naturally occurring proteins, where such variants are homologous or substantially similar to the naturally occurring protein, and can be of an origin of the same or different species as the naturally occurring protein. In general, variant polypeptides have a sequence that has at least about 80%, usually at least about 90%, and more usually at least about 98% sequence identity with a differentially expressed polypeptide described herein. The variant polypeptides can be naturally or non-naturally glycosylated, i.e., the polypeptide has a glycosylation pattern that differs from the glycosylation pattern found in the corresponding naturally occurring protein.

Fragments of the polypeptides disclosed herein, particularly biologically active fragments and/or fragments corresponding to functional domains, are of interest. Fragments of interest will typically be at least about 10 aa to at least about 15 aa in length, usually at least about 50 aa in length, and can be as long as 300 aa in length or longer, but will usually not exceed about 1000 aa in length, where the fragment will have a stretch of amino acids that is identical to a polypeptide encoded by a polynucleotide having a sequence of any one of the polynucleotide sequences provided herein, or a homolog thereof. A fragment "at least 20 aa in length," for example, is intended to include 20 or more contiguous amino acids. In this context "about" includes the particularly recited value or a value larger or smaller by several (5, 4, 3, 2, or 1) amino acids.

A polypeptide marker can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast higher plant, insect, and mammalian cells.

Polypeptides can be prepared and used for raising antibodies for experimental, diagnostic, and therapeutic purposes. Antibodies may be used to identify MS lesions or subtypes of lesions. These antibodies are specific to an epitope on the polypeptide, and can precipitate or bind to the corresponding native protein in a cell or tissue preparation or in a cell-free extract of an in vitro expression system.

The antibodies may be utilized for immunophenotyping of cells and biological samples, e.g. a needle biopsy. Monoclonal antibodies directed against a specific epitope, or combination of epitopes, will allow for the screening of cell populations potentially containing the marker. Various techniques can be utilized using monoclonal antibodies to screen for cellular populations expressing the marker(s), and include RIA, ELISA, immunohistochemistry, magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed into biologic fluids, and the like.

In many embodiments, the level of a subject polypeptide is measured. By measured is meant qualitatively or quantitatively estimating the level of the polypeptide in a first biological sample either directly (e.g. by determining or estimating absolute levels of polypeptide) or relatively by comparing the levels to a second control biological sample. In many embodiments the second control biological sample is obtained from an individual not having MS. As will be appreciated in the art, once a standard control level of gene expression is known, it can be used repeatedly as a standard for comparison.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Experimental

Proteomic Analysis of Active Multiple Sclerosis Lesions Reveals Therapeutic Targets Laser-capture microdissection (LCM) and proteomics were used to identify proteins unique to three major types of multiple sclerosis (MS) lesions: acute plaque (AP), chronic active plaque (CAP) and chronic plaque (CP). Comparative proteomic profiles identified tissue factor (TF) and protein C inhibitor (PCI) within CAP samples, suggesting dysregulation of molecules associated with coagulation. In vivo administration of the thrombin inhibitor hirudin or recombinant activated protein C (aPC) reduced disease severity in experimental autoimmune encephalomyelitis (EAE) and suppressed Th1 and Th17 cytokines in astrocytes and immune cells. Administration of mutant forms of recombinant aPC showed that both its anticoagulant and its signaling functions were essential for optimal amelioration of EAE. A proteomic approach illuminated potential therapeutic targets selective for specific pathological stages of MS and implicated participation of the coagulation cascade.

Here, we classified MS brain lesions into distinct histological types: acute plaque (AP), chronic active plaque (CAP) and chronic plaque (CP). We then isolated the lesions by LCM and performed saturated sequencing by mass spectrometry. We selected two candidate proteins, tissue factor (TF) and protein C inhibitor (PCI), via an analysis using a computer-guided system. We then validated their potential therapeutic roles in experimental autoimmune encephalomyelitis (EAE). We also studied the cellular and molecular mechanism of how activated protein C (aPC), an intrinsic inhibitor of PCI, ameliorates EAE. These findings emphasize how lesion-specific proteomic profiling of diseased tissue from MS patients can identify potential therapeutic targets. In addition, we reveal the extensive interface between the coagulation system and brain inflammation.

Results

Histological characterization of MS lesions. MS brain autopsy samples from patients with different clinical subtypes (Table 1) were evaluated by staining with Hematoxylin and Eosin (H&E), Luxol Fast Blue (LFB) and immunohistochemistry (IH). Lesions with florid parenchymal and perivascular inflammatory cell infiltration, abundant astroglial hypertrophy, myelin fragmentation, edema and ongoing demyelination with indistinct margins were classified as AP (FIG. 1a-c). CAP lesions had chronic demyelination, sharply defined margins and recent areas of inflammatory demyelination at the edges (FIG. 1d-f). CP lesions had areas of demyelination with well-demarcated borders and abundant astrogliosis but few or no inflammatory cells (FIG. 1g-i). Age-matched control brain samples were analyzed similarly and were devoid of CNS abnormalities.

Figure 2:
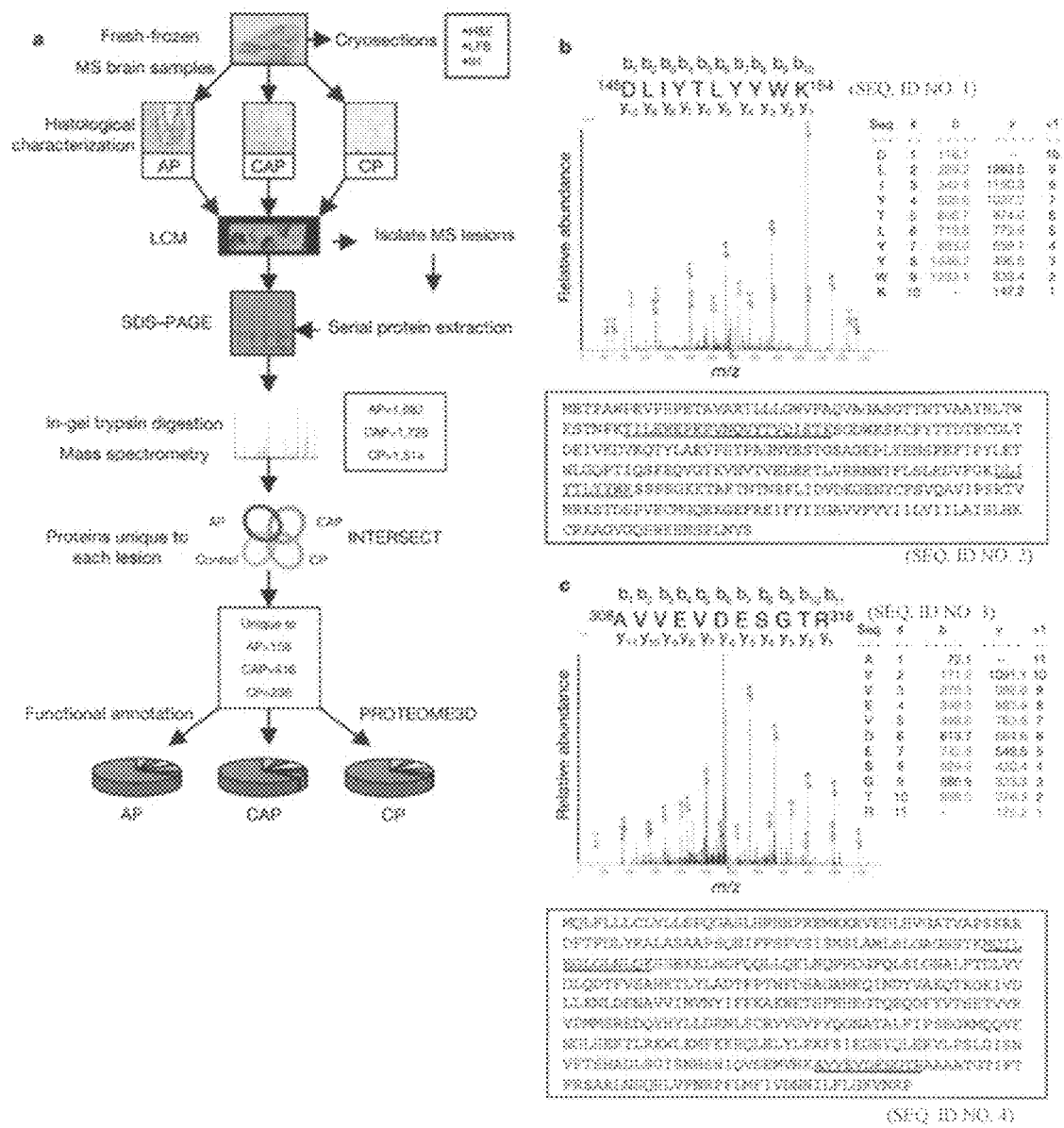
FIG. 2: a) Schematic procedure of the proteomic analysis of MS lesions. b) Representative tandem mass spectra of peptide(s) identified from b) TF or c) PCI from CAP samples. Sequences of identified peptides are shown above the mass spectra and underlined in the protein sequence; $b_n$ or $y_n$ denotes the ion generated by cleavage of the peptide bond after the nth amino acid from the amino terminus or the carboxyl terminus; identified b or y ions are shown in boldface letters; and values of m/z (mass/charge) for ions are indicated in the table.

Proteomic profiling of MS lesions. We compared the different histological stages of MS lesions by proteomics analysis to determine their global protein expression profiles. LCM enabled selective isolation of MS lesions from the adjacent white matter from the same tissue blocks evaluated for histological characterization. Samples isolated by LCM were separately analyzed by nano-liquid chromatography and tandem mass spectrometry (FIG. 2a). To ascertain reliable protein identification, we used the criteria of stringent mass tolerance and eliminated false positive proteins by searching against a forward and reverse human protein database. Furthermore, to enhance maximal protein detection coverage, MS samples were analyzed repeatedly by mass spectrometric analysis (4-7 times) until a saturation point was reached. Analysis of control, AP, CAP and CP samples yielded a total of 2,574 proteins with high confidence. Among these, 2,302 proteins were related to MS samples (three types of lesions combined), and 1,492 proteins belonged to control samples (see Table 3 for a complete listing). For individual MS lesion types we identified 1,082, 1,728 and 1,514 proteins for AP, CAP and CP samples respectively (Table 2). To our knowledge this is the largest and the most comprehensive proteome of MS brain lesions characterized to date (Tables 3 and 5).

CAP expresses coagulation proteins. Following mass spectrometric protein identification, we utilized the INTERSECT software program to determine proteins specific to each MS lesion type. There were 158, 416 and 236 proteins unique to AP, CAP and CP (Table 4). We then applied the PROTEOME-3D software to assign biological functions and sub-cellular localization to these proteins. The analysis revealed that proteins of unknown function made up more than half of the unique proteins identified in all three MS lesion types. Of the proteins with known function, structural proteins, adhesion molecules, cell surface receptors and components of channels were among the most numerous (6% or greater). They were followed by proteins involved in the cell cycle, in synaptic transmission, in cellular signaling and in the components of the machinery for transcription and translation (2-6%). Least numerous were proteins with functions associated with molecular chaperones and cellular metabolism (<2%). Interestingly, the analysis revealed five proteins involved in coagulation: Tissue Factor (TF), protein C inhibitor (PCI), thrombospondin, Fibronectin and vitronectin (FIG. 2b, c). These coagulation proteins were unique to CAP samples.

Thrombin inhibition attenuates EAE. TF, a coagulation factor, is expressed in monocytes and astrocytes during inflammation and promotes proinflammatory thrombin signaling via Protease Activated Receptor (PAR) family of proteins. PCI is a serum protein that accumulates in the CAP lesions probably secondary to the disruption of the blood-brain barrier during neuroinflammation. PCI inhibits aPC. aPC also signals through PAR-1 and endothelial protein C receptor (EPCR). Despite sharing a common signaling pathway with procoagulant TF, aPC is an anticoagulant with cytoprotective properties. The combined presence of TF and PCI suggests proinflammatory thrombin formation and suppression of protein C (PC) pathway in CAP lesions.

Figure 3:
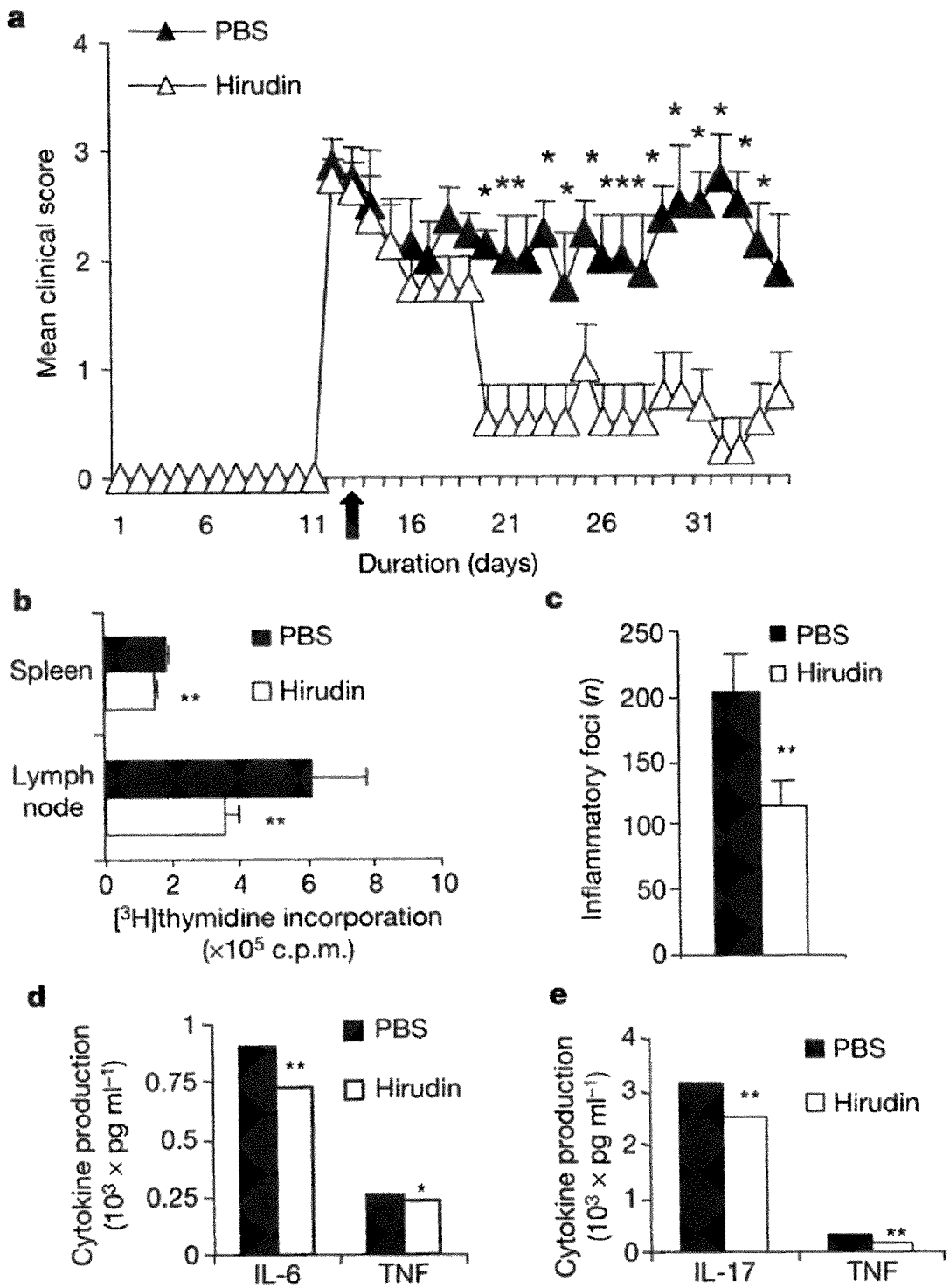
FIG. 3: Thrombin inhibition suppresses inflammation in EAE. a) Mean clinical scores±SEM of EAE mice treated with PBS (black) or recombinant hirudin (white) (10 mg/kg) (n=10/group) at the peak of disease (arrow) ($p<0.05$, Mann-Whitney analysis). b) In vitro proliferation rates of splenocytes and lymph node cells activated with PLP (20 µg/ml) and cytokine production from d) splenocytes and e) lymph node cells of PBS or hirudin-treated mice. Mean±SEM. *$p<0.05$, <0.02 (t test) (From triplicate culture wells). c) Quantitation of inflammatory lesions from brain and spinal cord of EAE mice treated with PBS or hirudin (n=5/group). Data represents means±SEM ($p<0.01$).
Figure 4:
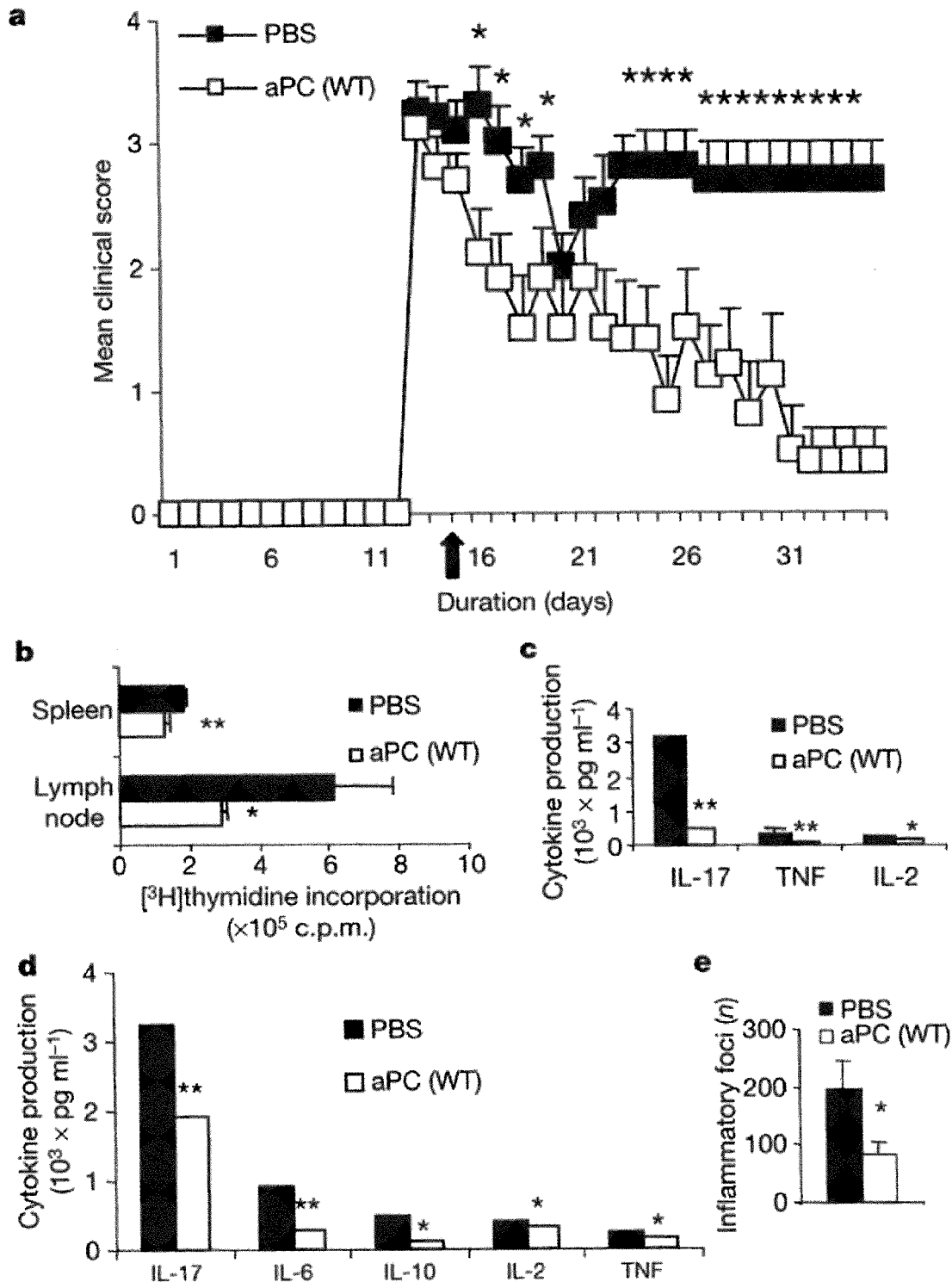
FIG. 4: aPC modulates Th1 and Th17 responses in EAE. a) Mean clinical scores±SEM of EAE mice treated with PBS (black) and aPC (white) at maximal paralysis (arrow) ($p<0.05$, Mann-Whitney analysis); b) proliferation rates of splenocytes and lymph node cells following activation with PLP peptide in culture and cytokine levels of c) lymph nodes and d) splenocytes from PBS and aPC-treated EAE mice. Means±SEM (pg/ml) (*$p<0.05$, **$p<0.02$, t test) e) Quantitation of inflammatory foci from paraffin-embedded sections from brain and spinal cord of EAE mice treated with PBS or aPC. Data represent mean±SEM, ($p<0.05$, t test).

To test the role of thrombin signaling during neuroinflammation, SJL/J mice that had been immunized with myelin proteolipid protein ($PLP_{139-151}$) peptide were treated daily with either intravenous injection of the thrombin inhibitor hirudin (Refludan, recombinant lepirudin, Berlex), or with phosphate buffered saline (PBS), at the peak of clinical disease. Mice treated with hirudin showed dramatic improvement of disease severity (FIG. 3a). This was accompanied by decreased immune cell proliferation (FIG. 3b) and suppression of cytokines IL-6, tumor necrosis factor (TNF) and IL-17 (FIG. 3d, e). There were no differences in the production of IL4, IL-10, IL-12 and interferon-γ (IFN-γ) cytokines between the vehicle-treated and the hirudin-treated groups. Hirudin had no effect on relapse rates or disease course. The brains and spinal cords of mice treated with hirudin showed fewer inflammatory foci (FIG. 3c). Amelioration of EAE by hirudin treatment was observed only up to day 35, probably secondary to development of autoantibodies against hirudin.

aPC administration ameliorates EAE. aPC has anti-inflammatory and anti-apoptotic functions and its therapeutic benefits have previously been observed in meningococcemia and in SIRS (Systemic Inflammatory Response Syndrome). The presence of PCI in CAP samples and evidence of low serum levels of PC in MS patients suggest suppression of the PC pathway during MS. To determine the effects of aPC during neuroinflammation, we induced EAE in 7-8 week-old SJL/J mice and treated them with either recombinant murine aPC (0.2 mg/kg) or vehicle (PBS) beginning at the peak of disease. During the course of EAE, mice treated with aPC showed significant amelioration of disease severity (FIG. 4a). Treatment had no effect on relapse rates nor did it after the disease course. This effect was accompanied by decreased immune cell proliferation in splenocytes and lymph node cells (FIG. 4b) and inhibition of Th1 and Th17 cytokines in aPC-treated mice (FIG. 4c, d). Additionally, fewer inflammatory foci were observed in the CNS tissue of EAE mice treated with aPC (FIG. 4e).

Figure 5:
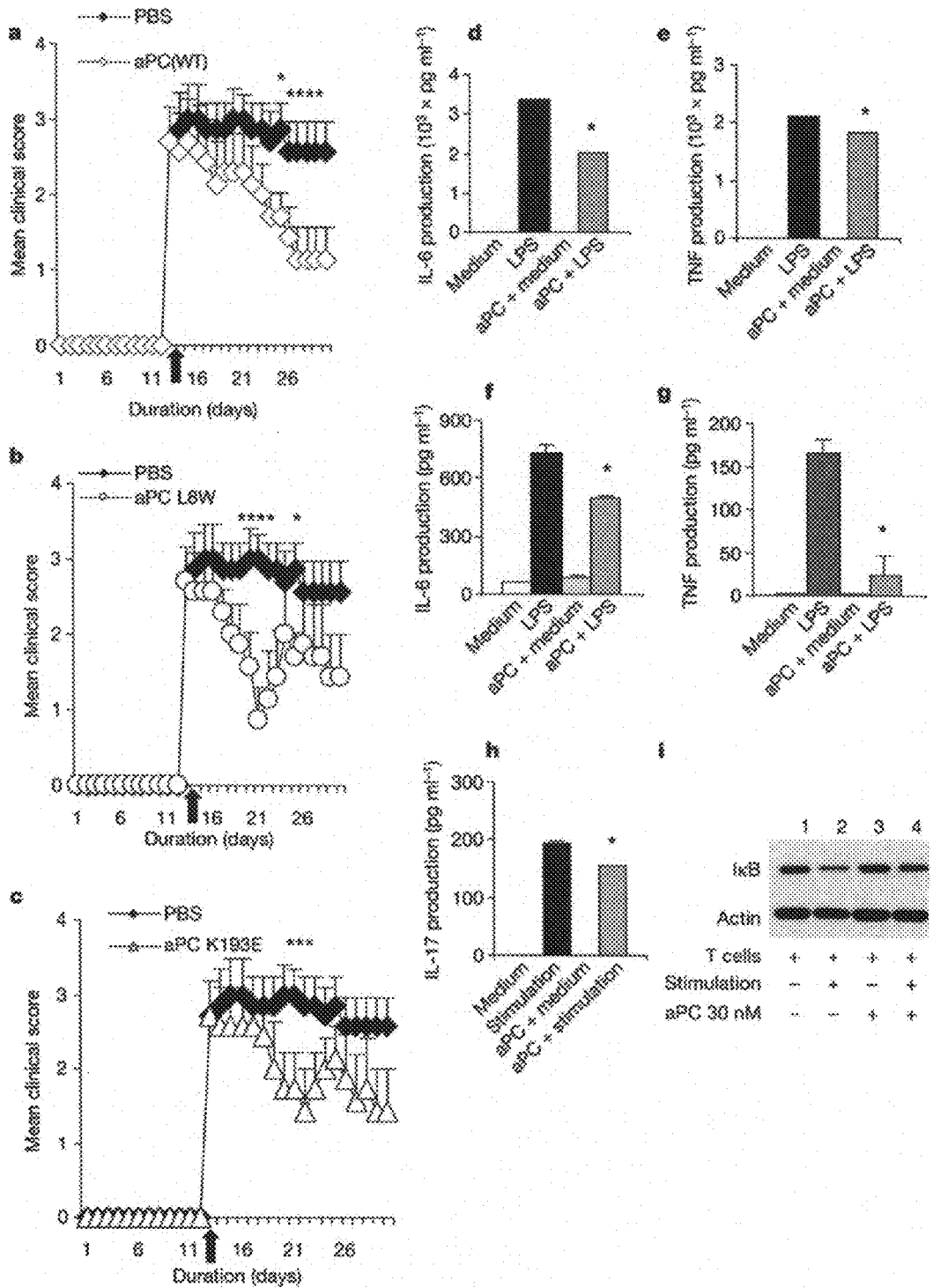
FIG. 5: Molecular mechanism of aPC during EAE. SJL/J mice with established EAE (n=7/group) were treated with (arrow) PBS or aPC-WT (a), aPC-L8W (b) or aPC-K193E (c)(0.46 mg/kg). Mean clinical scores SEM (p*<0.05, Mann-Whitney analysis). d-h) Macrophages (d, e), primary astrocytes (f, g) or purified T cells (h) were pre-treated with recombinant murine aPC-WT (30 nM) and activated with LPS (100 ng/ml) (d-g) or CD3/CD28 (5 µg/ml) (h) and cytokine levels were measured from culture supernatant. Means±SE (pg/ml) ($p<0.05$, t test). i) Immunoblot of total cell lysate (50 pg) from purified T cells treated with aPC (30 minutes time point) probed with anti-IκB-α.

Molecular mechanism of aPC during EAE. aPC functions both as an anticoagulant and a signaling molecule. Structure-function studies have identified the domain of aPC required for its anticoagulant function as distinct from its signaling function. To determine whether the amelioration of EAE by aPC treatment is mediated through anti-coagulant or signaling functions we induced EAE in SJL/J mice and treated with two recombinant aPC mutants, aPC-L8W and aPC-K193E. One mutant, aPC-L8W, retains anticoagulant properties but lacks PAR-1 signalling due to the defective interaction with its receptor EPCR at L8. The other mutant, aPC-K193E, mainly participates in PAR-1 signalling and lacks anticoagulant activities. The clinical status of the mice treated with aPC mutants were compared against those treated with either vehicle (PBS) or aPC wild type (WT). Mice treated with aPC-L8W and aPC-K193 showed significant amelioration early in the disease course (days 20-25) whereas mice treated with aPC-WT showed improvement in the latter part of disease course (days 25-30)(FIG. 5a-c). These data suggest that both activities of aPC may be required for maintaining an extended effect in this model.

To understand the effects of aPC on CNS and immune cells, we separately isolated peritoneal macrophages, astrocytes and T cells and activated them in vitro with either lipopolysaccharide (LPS) or CD3/CD28 following pre-treatment with recombinant murine aPC. Activated macrophages and astrocytes treated with aPC produced less IL6 and IL17 (FIG. 5d-g). Similarly, low levels of IL17 were detected in T cells exposed to aPC (FIG. 5h)., These data suggest that aPC suppresses inflammation in both the CNS and the periphery.

Since aPC suppressed NF-κB signaling during neuronal injury, we analyzed protein extracts from cultured T cells treated with murine aPC in cell activation assays by Western blot analysis. The results demonstrate less IκB breakdown in cells treated with aPC. This implies inhibition of NF-κB signalling by aPC.

This study provides the first ever information on large-scale protein identification from highly characterized MS brain lesions. Proteomic expression profiling of MS brain lesions has identified several candidate therapeutic targets. Reversing the physiological effects of two of these newly implicated proteins (TF and PCI) ameliorates disease in EAE. A parallel approach in identification of targets in EAE had previously led to development of new therapies in MS as in the case of Natalizumab which targets a critical integrin involved in homing of monocytes to the inflamed brain. Thus, this exercise has precedents in leading ultimately to new and effective therapies in MS.

Brück and Lucchinelti have classified active MS lesions according to their distinct histological and immunocytological characteristics (Lassmann et al. (2001) Trends Mol Med 7:115-21). The proteomic analysis of MS lesions illuminates the dynamic biological events that influence lesion development and pathogenesis. These proteomics techniques have been refined in the present invention to analyze specific areas in MS tissues (e.g. normal appearing white matter, areas of oligodendrocyte destruction) in order to identify proteins unique to these particular regions of interest.

The reversal of neurological deficits in EAE by administration of thrombin inhibitor and aPC demonstrates several new options for MS therapy. Heparin therapy was previously shown to improve symptoms during MS relapses and active EAE (see Maschmeyer et al. (1961) Bulletin of the Los Angeles Neurological Society 165-71; and Lider et al. (1989) J Clin Invest 83, 752-6), but treating MS patients with an anticoagulant such as hirudin is not optimal because of the increased risk of bleeding. Serum of EAE mice-treated with hirudin also showed the presence of anti-hirudin antibodies, which may have interfered with the protective effects of hirudin during EAE.

However, aPC provides a useful drug for therapy in MS, which may be further improved through the use of an aPC variant with reduced bleeding potential (see Mosnier et al. (2007) Blood 109, 3161-72; and Bernard et al. (2001) N Engl J Med 344:699-709). Experiments utilizing function-specific aPC mutants described herein demonstrate that both the anticoagulant and signalling properties of aPC ameliorate EAE, perhaps through different mechanisms. One explanation consistent with our findings centers on PAR-1 activation, such that either sending a cytoprotective signal (through EPCR and PAR-1 via aPC-K193E) or inhibiting the generation of thrombin (via aPC-L8W, and thus suppressing its pro-inflammatory signals through PAR-1) is independently sufficient to improve function in EAE.

We used the approach of systems biology to identify the molecular composition of the proteins in defined MS lesions. The lesion-specific proteome reveals. a "New World" with unique proteins identified in all three MS lesions. Proteins like those of the coagulation cascade are clearly playing new and unexpected pathobiological roles. The intersection of the coagulation cascade and inflammation in MS is the first of many new discoveries emerging from this catalogue of proteins. These proteomes constitute a vocabulary for the biological language whose rules and structures allow understanding of the disease.

Methods

All solvents, high performance liquid chromatography (HPLC) or mass spectrometry grade, reagents for histology were from Fisher (New Jersey, USA). Metal-rim slides and micro centrifuge tube for LCM were from MMI (Knoxville, Tenn., USA). Recombinant murine aPC, recombinant human aPC wild type (aPC-WT) and mutants (aPC-L8W and aPC-K193E) were generously provided by Lilly Research Laboratories. Protease inhibitor cocktail tablets were from Roche Applied Science (Mannheim, Germany). ABC kit, secondary antibodies (biotinylated horseradish peroxidase conjugates) and Diaminobenzidine were from Vector Inc. (Burlingame, Calif. USA). Monoclonal anti-GFAP (Glial fibrillary acidic protein), anti-CD3, anti-CD45 and anti-CD68 were from Dako Cytomation (Cabinteria, Calif.) and anti-CD 28 was from BD Biosciences. Rabbit polyclonal antibodies against IκB-α and β actin were from Cell Signaling and Sigma, respectively. Monoclonal anti-PLP was prepared as described previously.

Human brain samples from MS cases and normal controls. Fresh frozen MS and normal control brain samples were obtained at autopsy under an IRB approved protocol. MS brain samples and accompanying paraffin-embedded sections were kindly provided by Dr. C. S. Raine. Normal control samples were obtained from the University of Washington Alzheimer's disease brain consortium. Samples were harvested, rapidly frozen and stored at −80° C. All samples were obtained from the cerebral hemispheres.

Histopathological characterization and classification of MS lesions. Unfixed, frozen brain tissue from MS and control samples were partially thawed and ~1 cm tissue blocks were embedded in OCT compound (Sakura Finetek, USA). Frozen blocks were cut into 6 μM cryosections, then fixed in acetone briefly and analyzed by H&E, LFB and IH staining using antibodies against PLP, GFAP, CD3, CD45 and CD68 as previously described by Chabas et al. (2001) Science 294: 1731-5. MS lesions were classified according to the criteria used by Lock et al. (2002) Nat Med 8:500-8. Normal control brain samples were ruled out for obvious CNS pathology.

Isolation of MS plaques by LCM and sample preparation. The LCM microscope and laser system were from MMI Systems (Geneva, Switzerland). MS lesions were isolated from samples (frozen blocks) used for histological characterization. 15 μM sections were cut on MMI membranes, briefly fixed in 75% ethanol and MS lesions were then isolated by LCM as previously described (Bagnato et al. (2007) Molecular & Cellular Proteomics 6, 1088-102). MS lesions from 400 tissue sections were isolated and extracted first with modified RIPA buffer (10 mM Tris-HCl, pH 7.5, 150 mM NaCl, 0.1% SDS, 1% Triton X100, 1% deoxycholate, 5 mM EDTA, supplemented with protease inhibitor cocktail) and subsequently with 2% SDS buffer (62.5 mM Tris-HCl, pH7.5, 2% SDS) for 15 mins each at 65° C. White matter from the control samples was also isolated in a similar manner.

In-gel trypsin digestion, nano liquid chromatography and tandem mass spectrometry. Protein extracts (100 μg per sample) from MS and control brain samples were resolved by 1-dimensional SDS-PAGE using a 4-12% NuPAGE gel (Invitrogen, San Diego, Calif.) and stained with Coomassie Brilliant Blue G-250. Protein bands (20 per sample) were then digested with trypsin and peptides were then extracted as described (Hwang et al. (2006) Molecular & Cellular Proteomics 5, 1131-45). Tryptic peptides were analyzed using an LTQ linear ion trap mass spectrometer (Thermo Finnigan, San Jose, Calif.) equipped with a commercial nanospray source (Thermo Finnigan). Samples were loaded into an in-house $C_{18}$ micro column (100-μm inner diameter, 360-μm outer diameter, 10-cm length, 5-μm bead size, 100-Å pore size, Column Engineering Inc., Ontario, Canada) by a microautosampler (Famos-Dionex, Sunnyvale, Calif.) and separated by an Agilent 1,100 high performance binary pump. Peptides were loaded for 20 mins with solvent A (5% acetonitrile, 0.4% acetic acid and 0.005% heptafluorobutyric acid) at a flow rate of ~200 nl/min by flow splitting. The solvent gradient of HPLC was linear from 95% solvent A to 30% solvent B (100% acetonitrile, 0.4% acetic acid, and 0.005% heptafluorobutyric acid) for 45 mins. The column was then regenerated by 80% solvent B for 10 mins and 100% solvent A for 10 mins. The eluent was introduced directly into an LTQ mass spectrometer via electrospray ionization. Each full mass spectrometric scan was followed by a five tandem mass spectrometry scan of the most intense ion with data-dependent selection using the dynamic exclusion option (Top 5 method). Dynamic exclusion features were enabled to maximize the fragmentation of low abundance peptide ions. Sample loading, solvent delivery and scan functions were obtained by XCalibur software (Thermo Finnigan). Each sample was analyzed 4-7 times by mass spectrometry.

Database searching and data processing. Data obtained from each gel band generated a .dat file and was searched independently against a non-redundant human protein database (56,709 entries as of Dec. 1, 2004, Advanced Biomedical Computing Center) using the SEQUEST algorithm, resulting in one .html output file. All .html files from each lesion type (AP, CAP, CP) were combined using the INTERACT program. They were then filtered using the following criteria: peptide mass tolerance of 2.0 with differential modification of +16 for oxidized methionine, +80 for phosphorylated serine, threonine and tyrosine, cross-correlation (Xcorr) of 1.9, 2.2, and 3.7 for 1+, 2+, and 3+ charge state peptides respectively and delta correlation (dCn) score greater than or equal to 0.1, excluding single peptide ID. False positive rates were estimated by searching a subset of AP, CAP, CP and control samples against a concatenated forward and reverse human protein database using the formula: False Positive (%)=number of reverse peptide Ids×100/number of forward peptide Ids, based on representative subsets of each category (Table 2).

Protein quantitation. Semi-quantitative protein abundance was estimated by spectral count (SC). SC=the number of tandem mass spectrometric spectra confidently assigned to the protein, as previously defined.

Identification of proteins unique to MS lesions and functional annotation. We used software INTERSECT to determine proteins unique to each lesion type. GO (gene ontology) classification and software PROTEOME-3D were then applied to assign biological functions and sub-cellular localization of these proteins.

EAE induction, treatment with hirudin, aPC (WT and mutants), proliferation assays, cytokine analysis and quantitative histopathology. Mice were maintained in the Research Animal Facility at Stanford University. EAE was induced in 7-8 week old SJL/J female mice by subcutaneous immunization with 100 μg $PLP_{139-151}$ in emulsion. For hirudin or aPC treatment, EAE mice (n=10/group) were treated with daily intravenous injection of hirudin (10 mg/kg) or mouse recombinant aPC-WT (0.2 mg/kg) at the peak of disease and compared with PBS treated group. Mice were assessed daily for clinical signs of EAE and scored according to: 0, no clinical disease; 1, tail weakness; 2, hindlimb weakness; 3, complete hindlimb paralysis; 4, hindlimb paralysis and some forelimb weakness; 5, moribund or dead.

Recombinant human aPC-WT and mutants (aPC-L8W and aPC-K193E) were prepared as described by Grinnell et al (2007) Critical Care Medicine (suppl). These aPC variants have the following properties on aPTT and PAR-1 signaling function: aPC-WT: aPTT (relative activity)=1, PAR-1 (relative activity)=1, aPC-L8W: aPTT=1, PAR-1=0.02 and aPC-K193E: aPTT=0.03, PAR-1=1. EAE mice (n=7/group) were treated with daily intravenous injection of recombinant human aPC-WT, aPC-L8W, aPC-K193E (0.46 mg/kg) or PBS (control group) at the time of maximal paralysis and assessed daily until day 30.

In vitro immune cell proliferation and cytokine analysis were performed as previously described (Ousman et al. (2007) Nature 448, 474-9). Briefly, splenocytes and lymph node cells harvested from EAE experiments were cultured in flat-bottomed, 96-well plates at a concentration of $0.5 \times 10^6$ cells/well in stimulation media (RPMI 1640 supplemented with 2 mM L-glutamine, 1 mM sodium pyruvate, 0.1 mM non-essential amino acids, 100 U/ml² Penicillin, 0.1 mg/ml² streptomycin, 0.5 μM 2-mercaptoethanol and 10% fetal calf serum) and activated with $PLP_{139-151}$ peptide (5-20 μg/ml). To determine proliferation rates, cultures were pulsed with ($^3$H)-Thymidine (1 μCi per well) following 72-hour culture and harvested 18 hours later onto filter paper. The counts per minute (cpm) of incorporated $^3$H-Thymidine were read using a beta counter. Cytokine levels (IL-2, IL-4, IL-6, IL-10, IL-12p40, IL-17, IFN-γ, TNF) were measured from the supernatant of cultured cells using anti-mouse OPTEIA ELISA kits (BD Pharmigen).

For histopathological analysis, brains and spinal cord of EAE mice were fixed in 10% formaldehyde. 6 μM thick paraffin sections were stained with LFB and H&E and the number of inflammatory foci within the brain and spinal cord were quantified by a neuropathologist who was blinded to the treatment and clinical parameters of the mice.

In vitro Immune cell activation assays and cytokine analysis. T lymphocytes were isolated from pooled splenocytes and lymph node cells from 8 week-old naïve SJL/J mice by negative selection (Pan T cell isolation kit, Miltenyi Biotech). Cells were pre-treated with 30 nM recombinant murine aPC for 15 mins at 37° C. followed by activation with CD3/CD28 (5 μg/ml) coated on 12 well plates. Cells were cultured at $5 \times 10^6$ cells/ml concentration in stimulation media. Culture plates were harvested at different time points (15 min-96 hours) and cytokine levels were measured from culture supernatant by ELISA.

Primary peritoneal macrophages were isolated from naïve 8-9 weeks old SJL/J mice following intraperitoneal injection of thioglycollate (BD Diagnostic Systems) and cultured in complete medium (DMEM supplemented with 10% fetal bovine serum, 1 mM sodium pyruvate, 100 μM penicillin and 0.1 mg/ml streptomycin). Cells ($1 \times 10^6$ cells/ml) were treated with 30 nM recombinant murine aPC for 15 minutes, then activated with LPS 100 ng/ml (Sigma), harvested at different time points (15 min-72 hours), and cytokine levels were measured.

Astrocyte culture. Astrocytes were cultured from brain of one-day-old SJL/J pups as described previously. Briefly, the cerebral cortices from pups were minced, cells were disrupted by passing through a filter and cultured in complete DMEM. Purified astrocytes (50-80% confluent) were treated with 30 nM recombinant murine aPC for 15 minutes and activated with 100 ng/ml LPS (Sigma). Cells were harvested at 4, 24, 48 and 72-hours, and supernatant were analyzed by ELISA for cytokine production.

Western blot analysis. For NF-κB activation, total cell lysate from purified T cells treated with aPC were analyzed by SDS-PAGE, transferred to PVDF membrane, probed with antibodies against IκB-α, and β-actin and the signal was visualized by enhanced chemiluminescence.

Statistical analysis. Data are presented as means±SEM. When data were parametric, a t-test (n=2 groups) was used to detect between-group differences. When data were non-parametric, a Mann-Whitney U test was used for comparison between groups (n=2 groups). A p value of <0.05 or lower was considered significant. Error bars in FIG. 3$d$, $e$, FIG. 4$c$, $d$ and FIG. 5$d$, $e$ are not discernible due to their small size.

TABLE 1

Characteristics of the MS patients and controls in the study

| | Age/gender | Type of MS | Disease duration | Prior treatment | Lesion type | Cause of death | Autopsy interval |
|---|---|---|---|---|---|---|---|
| MS1 | 42/F | Acute | 2 wk | None | AP | Respiratory failure | 12 h. |
| MS2 | 54/F | Acute | 2½ mo | Corticosteroids | AP | Respiratory failure | 12 h. |
| MS3 | 31/F | Chronic | 11 y | Corticosteroids | CAP | Respiratory failure | 1.5 h |
| MS4 | 27/F | Progressive | 10 y. | Corticosteroids | CAP | Broncho-pneumonia | 4 h. |
| MS5 | 47/M | Secondary Progressive | 20 y | Corticosteroids | CP | Respiratory failure | 24 h |
| MS6 | 46/M | Chronic progressive | 15 y | Lioresal Compazine | CP | Cardiac arrest | 4 h |
| Control 1 | 23/F | Fallopian tube cancer | N/A | N/A | | Respiratory failure | 12 h |
| Control 2 | 52/F | Ovarian cancer | N/A | N/A | | Respiratory failure | 15.5 h |

Two separate samples of brain lesions were obtained from MS1 and 2 and three separate samples were obtained from MS3-6 and normal control samples. None of the MS cases were treated with disease modifying agents. Full CNS autopsies were performed on all cases.

TABLE 2

Summary of the proteomic data

| | AP | CAP | CP | CTL |
|---|---|---|---|---|
| Peptide | 40,819 | 64,678 | 54,339 | 68,478 |
| Unique peptide | 6,321 | 10,143 | 8,967 | 8,991 |
| Protein* | 1,082 | 1,728 | 1,514 | 1,492 |
| Reverse peptide Ids | 39 | 34 | 10 | 12 |
| Forward peptide ids | 3612 | 4937 | 3687 | 4020 |
| False positive (%)** | 1.08 | 0.69 | 0.27 | 0.3 |

*Identification filtering criteria: Xcorr 1.9 (1+), 2.2(2+), 3.7(3+), dCn > 0.1, excluding trypsin, including keratin, excluding single peptide ID. The files used to compute false positive rate were searched against concatenated forward and reverse human database.
**Formula for the False Positive (%): number of reverse Ids × 100/number of forward Ids, based on representative subset of each category.

TABLE 3

PROTEINS UNIQUE TO AP

| Protein ID | Common Name |
|---|---|
| 2A5E_HUMAN | Serine/threonine protein phosphatase 2A |
| A3B1_HUMAN | Adapter-related protein complex 3 beta 1 subunit |
| AGRN_HUMAN | Agrin precursor |
| ANC1_HUMAN | Anaphase promoting complex subunit 1 |
| ASP2_HUMAN | Apoptosis stimulating of p53 protein 2 |
| AT10_HUMAN | ADAMTS-10 precursor Secreted |

TABLE 3-continued

PROTEINS UNIQUE TO AP

| Protein ID | Common Name |
| --- | --- |
| ATHA_HUMAN | Potassium-transporting ATPase alpha chain 1 |
| ATX7_HUMAN | Ataxin-7; Spinocerebellar ataxia type 7 protein |
| BAI2_HUMAN | Brain-specific angiogenesis inhibitor 2 precursor |
| BDH_HUMAN | D-beta-hydroxybutyrate dehydrogenase |
| CA17_HUMAN | Collagen alpha-1(VII) chain [Precursor] Basement membrane |
| CA1G_HUMAN | Collagen alpha 1 Type II membrane protein |
| CACP_HUMAN | Carnitine O-acetyltransferase Endoplasmic reticulum |
| CDA9_HUMAN | Protocadherin alpha 9 precursor |
| CHD1_HUMAN | Chromodomain-helicase-DNA-binding protein 1 |
| CHD2_HUMAN | similarity to CHROMODOMAIN HELICASE DNA-BINDING PR |
| CHD7_HUMAN | Chromodomain-helicase-DNA-binding protein 7 |
| CMGA_HUMAN | Chromogranin A precursor Neuroendocrine and endocrine |
| DCE2_HUMAN | Glutamate decarboxylase, 65 kDa isoform |
| DHE4_HUMAN | Glutamate dehydrogenase 2, mitochondrial precursor |
| DJA4_HUMAN | DnaJ homolog subfamily A member 4 Membrane-bound |
| E2F4_HUMAN | Transcription factor E2F4 Nuclear. |
| EFB1_HUMAN | Ephrin-B1 precursor Type I membrane protein |
| F20C_HUMAN | Protein FAM20C precursor |
| FGD1_HUMAN | Putative Rho/Rac guanine nucleotide exchange factor |
| FX30_HUMAN | F-box only protein |
| FXR1_HUMAN | Fragile X mental retardation syndrome related protein 1 |
| GCP6_HUMAN | Gamma-tubulin complex component 6; GCP-6 |
| GLR3_HUMAN | Glutamate receptor 3 precursor |
| GP80_HUMAN | Probable G protein-coupled receptor GPR80 |
| GTR3_HUMAN | Solute carrier family 2, facilitated glucose transporter |
| HB21_HUMAN | HLA class II histocompatibility antigen |
| HGF_HUMAN | Hepatocyte growth factor precursor |
| ITB4_HUMAN | Integrin beta-4 precursor Type I membrane protein |
| ITN1_HUMAN | Intersectin 1; SH3 domain-containing protein 1A |
| JAK1_HUMAN | Tyrosine-protein kinase JAK1 |
| LRR8_HUMAN | Leucine-rich repeat-containing protein 8 precursor |
| M3K1_HUMAN | Mitogen-activated protein kinase kinase kinase 1 |
| MINT_HUMAN | Msx2-interacting protein |
| MY15_HUMAN | Myosin XV |
| MYBA_HUMAN | Myb-related protein A |
| MYM1_HUMAN | Myomesin 1 (190 kDa titin-associated protein) |
| NAC1_HUMAN | Sodium/calcium exchanger 1 precursor |
| NAF1_HUMAN | Nef-associated factor 1 |
| NFX1_HUMAN | Transcriptional repressor NF-X1 |
| NI2M_HUMAN | NADH-ubiquinone oxidoreductase B22 subunit |
| NSD1_HUMAN | Nuclear receptor binding SET domain containing protein 1 |
| NU93_HUMAN | Nuclear pore complex protein Nup93 |
| NUKM_HUMAN | NADH-ubiquinone oxidoreductase 20 kDa subunit, mitochondr NO INFO NO INFO 23564 10 |
| O15065 | KIAA0358 protein; C: cytoplasm NO INFO NO INFO 176077 5.75 |
| O15081 | KIAA0376 protein NO INFO NO INFO 99803 5.07 |
| O60611 | Supervillin |
| O75042 | KIAA0454 protein |
| O75160 | KIAA0672 protein |
| O75163 | KIAA0676 protein |
| O75183 | KIAA0701 protein |
| O75691 | DRIM protein |
| O94896 | KIAA0804 protein |
| O95204 | Metalloprotease 1 |
| O96005 | Cleft lip and palate transmembrane protein 1 |
| P78524 | P126 |
| PAPG_HUMAN | Poly(A) polymerase gamma; PAP gamma |
| PAX3_HUMAN | Paired box protein Pax-3; HUP2 |
| PC16_HUMAN | Protocadherin 16 precursor Type I membrane protein |
| PCP_HUMAN | Lysosomal Pro-X carboxypeptidase precursor |
| PER3_HUMAN | Period circadian protein 3 |
| PHF6_HUMAN | PHD finger protein 6 |
| PKHD_HUMAN | Polycystic kidney and hepatic disease 1 precursor |
| Q13535 | FRAP-related protein; F: protein kinase activity |
| Q66M66 | Cdc42-associated guanine nucleotide exchange factor |
| Q68D12 | Hypothetical protein DKFZp781C0723 |
| Q68DP5 | Hypothetical protein DKFZp686B2031 |
| Q693C2 | Nonstructural protein 1; C: virion |
| Q6IMI5 | SULT1C3 splice variant a; F: sulfotransferase activity |
| Q6MZP7 | Hypothetical protein DKFZp686G04165 |
| Q6NY19 | FLJ46061 protein |
| Q6PK04 | MGC16597 protein |
| Q6ZRV8 | Hypothetical protein FLJ46051 |
| Q6ZSJ6 | Hypothetical protein FLJ45467 |
| Q6ZSS7 | Hypothetical protein FLJ45241 |
| Q6ZUD8 | Hypothetical protein FLJ43793 |

TABLE 3-continued

PROTEINS UNIQUE TO AP

| Protein ID | Common Name |
|---|---|
| Q6ZV52 | Hypothetical protein FLJ42981 |
| Q71RH2 | FP1188; C: integral to membrane |
| Q7KWM6 | Similar to Homo sapiens |
| Q7RTR0 | NOD6 |
| Q7Z7J6 | Actin alpha 1 skeletal muscle protein |
| Q86V20 | Family with sequence similarity 35 |
| Q8IUN3 | FLJ10157 protein |
| Q8IW51 | KIAA1458 protein |
| Q8IWG2 | Hypothetical protein LOC284001 |
| Q8IWV7 | Ubiquitin ligase E3 alpha-I; F: ligase activity |
| Q8IXS1 | ARHGAP20 protein |
| Q8IYQ7 | Threonine synthase-like 1 |
| Q8IZ48 | FBF1 protein |
| Q8N3R6 | Hypothetical protein DKFZp451G165 |
| Q8N442 | Hypothetical protein FLJ13220 |
| Q8N5D9 | Similar to spindlin; P: gametogenesis |
| Q8N6P1 | TMPIT protein |
| Q8N6Z5 | PTPN23 protein |
| Q8N970 | Hypothetical protein FLJ38285 |
| Q8N9C0 | Hypothetical protein FLJ37794 |
| Q8N9H0 | Hypothetical protein FLJ37160 |
| Q8NCD6 | Hypothetical protein FLJ90323 |
| Q8ND71 | hypothetical protein |
| Q8NDT2 | Hypothetical protein DKFZp547N2215 |
| Q8SSN9 | Similar to Homo sapiens |
| Q8TAI1 | Similar to LOC147447 |
| Q8TDM9 | Amplified in breast cancer 1 |
| Q8TEN9 | FLJ00154 protein |
| Q8TF60 | KIAA1941 protein |
| Q8WWZ8 | LZP; Hypothetical protein FLJ39116 |
| Q8WXX0 | Ciliary dynein heavy chain 7 |
| Q8WYL5 | HSSH-1L |
| Q8WYN8 | Ribosomal protein S27a |
| Q96CN6 | ADCK2 protein |
| Q96F76 | Putative RNA methyltransferase |
| Q96FZ8 | Citrate synthase, mitochondrial [Precursor] |
| Q96GK7 | Fumarylacetoacetate hydrolase domain containing 2A |
| Q96I57 | MYH7B protein |
| Q96JB1 | DNAH8 |
| Q96M34 | Hypothetical protein FLJ32859 |
| Q96Q04 | KIAA1883 protein |
| Q96QE4 | Hypothetical protein |
| Q96RD8 | GTP binding protein Rab1a |
| Q96RK0 | Capicua protein |
| Q9BZS0 | Kappa B and V(D)J recombination signal sequences binding prNO |
| Q9C0B7 | KIAA1746 |
| Q9HCD6 | KIAA1636 protein |
| Q9NQW1 | Secretory pathway component Sec31B-1 |
| Q9P2H0 | KIAA1377 protein |
| Q9P2J0 | KIAA1357 protein |
| Q9ULU2 | KIAA1127 protein |
| Q9UNJ2 | Myosin-IXa |
| Q9Y2I9 | KIAA0984 protein |
| Q9Y4F4 | KIAA0423 protein |
| R39B_HUMAN | small GTP-binding rab protein |
| RGE4_HUMAN | RAP guanine-nucleotide-exchange factor 4 |
| RH26_HUMAN | Rho-GTPase-activating protein 26 |
| RP2B_HUMAN | Ras-related protein Rap-2b |
| RRP5_HUMAN | RRP5 protein homolog; Programmed cell death protein 11 |
| RYR2_HUMAN | Ryanodine receptor 2 Integral membrane protein |
| S6A1_HUMAN | Sodium- and chloride-dependent GABA transporter 1 |
| SGCE_HUMAN | Epsilon-sarcoglycan precursor Type I membrane protein |
| SON_HUMAN | SON protein; SON3; Negative regulatory element-binding protein |
| SPCR_HUMAN | Spectrin beta chain, brain 4 Cytoplasmic |
| SRB1_HUMAN | Signal-regulatory protein beta-1 precursor; SIRP-beta-1 |
| SRB2_HUMAN | Signal-regulatory protein beta-2 precursor; SIRP-beta-2 |
| T172_HUMAN | TBP-associated factor 172; TAF-172 |
| T4AP_HUMAN | Trpc4-associated protein |
| TOP1_HUMAN | DNA topoisomerase I |
| TRP4_HUMAN | Short transient receptor potential channel 4 |
| U13A_HUMAN | Unc-13 homolog A |
| U13B_HUMAN | Unc-13 homolog B; Munc13-2 |
| UB13_HUMAN | Ubiquitin carboxyl-terminal hydrolase 13 |
| UGG2_HUMAN | UDP-glucose:glycoprotein glucosyltransferase 2 precursor |
| VATL_HUMAN | Vacuolar ATP synthase 16 kDa proteolipid subunit |

TABLE 3-continued

PROTEINS UNIQUE TO AP

| Protein ID | Common Name |
| --- | --- |
| Y296_HUMAN | Hypothetical zinc finger protein KIAA0296 |
| Z479_HUMAN | Zinc finger protein 479 |

TABLE 4

Proteins unique to CAP

| Protein ID | Common Name |
| --- | --- |
| 2A5D_HUMAN | Serine/threonine protein phosphatase |
| 5NTD_HUMAN | 5'-nucleotidase, ecto NO |
| A1M1_HUMAN | Adaptor-related protein complex |
| ABR_HUMAN | Active breakpoint cluster |
| AFAM_HUMAN | Afamin precursor; Alpha-albumin; |
| AFP2_HUMAN | Arfaptin 2; ADP-ribosylation |
| AKC1_HUMAN | Aldo-keto reductase family |
| ANC5_HUMAN | Anaphase promoting complex |
| ANRY_HUMAN | Ankyrin repeat domain |
| APC_HUMAN | Adenomatous polyposis coli |
| APXL_HUMAN | Apical-like protein; APXL |
| AR1A_HUMAN | Actin-related protein 2/3 |
| ARH2_HUMAN | rhoVrac guanine nucleotide |
| ASC_HUMAN | Apoptosis-associated speck-like protein |
| ASPH_HUMAN | Aspartyl/asparaginyl beta-hydroxylase Type |
| ATCY_HUMAN | Caytaxin; Ataxia Cayman |
| ATHL_HUMAN | Potassium-transporting ATPase alpha |
| ATND_HUMAN | Sodium/potassium-transporting ATPase beta-3 |
| ATPR_HUMAN | ATP synthase coupling |
| ATS6_HUMAN | ADAMTS-6 precursor; A |
| BAG3_HUMAN | BAG-family molecular chaperone |
| BC046405_1 | Hps5 protein [Mus |
| BGAL_HUMAN | Beta-galactosidase precursor Lysosomal. |
| BM02_HUMAN | UPF0185 protein BM-002 |
| BOR4_HUMAN | Cdc42 effector protein |
| BPEB_HUMAN | Bullous pemphigoid antigen |
| C10_HUMAN | Putative C10 protein |
| C3L1_HUMAN | Chitinase-3 like protein |
| CA11_HUMAN | Collagen alpha 1 |
| CA21_HUMAN | Collagen alpha 2 |
| CA25_HUMAN | Collagen alpha 2 |
| CA26_HUMAN | Collagen alpha 2 |
| CA36_HUMAN | Collagen alpha 3 |
| CADJ_HUMAN | Cadherin-19 precursor; UNQ478/PRO941; |
| CAFA_HUMAN | Chromatin assembly factor |
| CALD_HUMAN | hypothetical protein with |
| CALU_HUMAN | Calumenin precursor; Crocalbin; |
| CARC_HUMAN | Caspase recruitment domain |
| CCDA_HUMAN | Coiled-coil domain containing |
| CD82_HUMAN | CD82 antigen (Inducible |
| CDK5_HUMAN | Cell division protein |
| CDS2_HUMAN | Phosphatidate cytidylyltransferase 2; |
| CEBP_HUMAN | Cyclin-E binding protein |
| CEG3_HUMAN | Centaurin gamma 3 |
| CHP1_HUMAN | Calcium-binding protein p22; |
| CLP2_HUMAN | Calponin-2 (Calponin H2, |
| CLP3_HUMAN | Calponin-3 (Calponin, acidic |
| CN2A_HUMAN | cGMP-dependent 3', 5' -cyclic phosphodiesterase; |
| CN3B_HUMAN | cGMP-inhibited 3', 5' -cyclic phosphodiesterase |
| CN4A_HUMAN | cAMP-specific 3',5'-cyclic phosphodiesterase |
| CN4B_HUMAN | cAMP-specific 3',5'-cyclic phosphodiesterase |
| CNB3_HUMAN | Cyclic-nucleotide-gated cation channel |
| CNC3_HUMAN | Protein C14orf123; HSPC134; |
| COA2_HUMAN | Acetyl-CoA carboxylase 2 |
| COPD_HUMAN | Coatomer delta subunit |
| COPE_HUMAN | Coatomer epsilon subunit; |
| COPP_HUMAN | COATOMER BETA PRIME |
| COPZ_HUMAN | Coatomer zeta-1 subunit |
| COXJ_HUMAN | Cytochrome c oxidase |
| CP27_HUMAN | Cytochrome P450 27, |
| CSN6_HUMAN | COP9 signalosome complex |
| CT53_HUMAN | Hypothetical protein C20orf53 |
| CXA1_HUMAN | Gap junction alpha-1 |
| CYA5_HUMAN | Adenylate cyclase, type |

TABLE 4-continued

Proteins unique to CAP

| Protein ID | Common Name |
|---|---|
| DAB2_HUMAN | Disabled homolog 2 |
| DCD_HUMAN | Dermcidin precursor Secreted. |
| DD17_HUMAN | Probable RNA-dependent helicase |
| DESP_HUMAN | Desmoplakin (DP) Innermost |
| DHS1_HUMAN | Dehydrogenase/reductase SDR family |
| DJB6_HUMAN | DnaJ homolog subfamily |
| DLG5_HUMAN | Discs, large homolog |
| DPM1_HUMAN | Dolichol-phosphate mannosyltransferase; Dolichol-phosphate |
| DTNA_HUMAN | Dystrobrevin alpha Cytoplasmic. |
| DTX2_HUMAN | Deltex protein 2; |
| DUT_HUMAN | Deoxyuridine 5'-triphosphate nucleotidohydrolase, |
| EDD_HUMAN | Ubiquitin--protein ligase EDD |
| ENAH_HUMAN | Enabled protein homolog |
| ENH_HUMAN | Enigma homolog; Enigma-like |
| ENP1_HUMAN | Ectonucleoside triphosphate diphosphohydrolase |
| EWS_HUMAN | RNA-binding protein EWS |
| EXC7_HUMAN | Exocyst complex component |
| FABE_HUMAN | Fatty acid-binding protein, |
| FAK2_HUMAN | Protein tyrosine kinase |
| FBL2_HUMAN | Fibulin-2 precursor; C: extracellular |
| FINC_HUMAN | Fibronectin precursor Secreted; |
| FLR2_HUMAN | Leucine-rich repeat transmembrane |
| FOG1_HUMAN | Zinc finger protein |
| G128_HUMAN | Probable G protein-coupled |
| GBF1_HUMAN | Golgi-specific brefeldin A-resistance |
| GBGC_HUMAN | Guanine nucleotide-binding protein |
| GBP1_HUMAN | Interferon-induced guanylate-binding protein |
| GCP3_HUMAN | Gamma-tubulin complex component |
| GCST_HUMAN | Aminomethyltransferase, mitochondrial precursor |
| GDL1_HUMAN | Ganglioside-induced differentiation-associated protein |
| GL6S_HUMAN | N-acetylglucosamine-6-sulfatase precursor Lysosomal. |
| GLR2_HUMAN | Glutamate receptor 2 |
| GUAA_HUMAN | GMP synthase [glutamine-hydrolyzing] |
| HE47_HUMAN | Spliceosome RNA helicase |
| HEMZ_HUMAN | Ferrochelatase, mitochondrial precursor |
| HP28_HUMAN | 28 kDa heat- |
| HS47_HUMAN | 47 kDa heat |
| HXA4_HUMAN | Homeobox protein Hox-A4 |
| ICAL_HUMAN | Calpain inhibitor NO |
| IDHG_HUMAN | Isocitrate dehydrogenase [NAD] |
| IF2A_HUMAN | Eukaryotic translation initiation |
| IF31_HUMAN | Eukaryotic translation initiation |
| IKKA_HUMAN | Inhibitor of nuclear |
| IM44_HUMAN | Import inner membrane |
| IP3K_HUMAN | Inositol-trisphosphate 3-kinase A; |
| IPO9_HUMAN | Importin 9; Imp9; |
| IPPD_HUMAN | Dopamine- and cAMP-regulated |
| IPSP_HUMAN | Plasma serine protease |
| IRF6_HUMAN | Interferon regulatory factor |
| IRS2_HUMAN | Insulin receptor substrate-2; |
| IVD_HUMAN | Isovaleryl-CoA dehydrogenase, mitochondrial |
| JMJ_HUMAN | Jumonji protein; Jumonji/ARID |
| K2C3_HUMAN | Keratin, type II |
| KCRM_HUMAN | Creatine kinase, M |
| KCRS_HUMAN | Creatine kinase, sarcomeric |
| KF11_HUMAN | Kinesin-like protein KIF11 |
| KF3A_HUMAN | Kinesin-like protein KIF3A |
| KF4A_HUMAN | Chromosome-associated kinesin KIF4A |
| KFP3_HUMAN | Kinesin-associated protein 3; |
| KHL2_HUMAN | Kelch-like protein 2; |
| KMLS_HUMAN | Myosin light chain |
| KPCB_HUMAN | Protein kinase C, |
| KPCE_HUMAN | Protein kinase C, |
| KPCO_HUMAN | Protein kinase C, |
| KPR2_HUMAN | Ribose-phosphate pyrophosphokinase II |
| KV1A_HUMAN | Ig kappa chain |
| LAP1_HUMAN | Leucine-rich repeat-containing protein |
| LCF3_HUMAN | Long-chain-fatty-acid--CoA ligase 3; |
| LD6B_HUMAN | L-lactate dehydrogenase A-like |
| LGMN_HUMAN | Legumain precursor; Asparaginyl |
| LMA1_HUMAN | Laminin alpha-1 chain |
| LPA3_HUMAN | Liprin-alpha 3 Cytoplasmic. |
| LUM_HUMAN | Lumican precursor Secreted; |
| LY6H_HUMAN | Lymphocyte antigen Ly-6H |
| MER1_HUMAN | Mammalian ependymin related |
| MIME_HUMAN | Mimecan precursor NO |

TABLE 4-continued

Proteins unique to CAP

| Protein ID | Common Name |
| --- | --- |
| MLEG_HUMAN | Myosin light chain |
| MLEY_HUMAN | Myosin light chain |
| MLRA_HUMAN | Myosin regulatory light |
| MMAA_HUMAN | Methylmalonic aciduria type |
| MPK4_HUMAN | Dual specificity mitogen-activated |
| MSAP_HUMAN | MIR-interacting saposin-like protein |
| MSLN_HUMAN | Mesothelin precursor Attached |
| MTR1_HUMAN | Myotubularin-related protein 1 |
| MTR3_HUMAN | Myotubularin-related protein 3; |
| MTRR_HUMAN | Methionine synthase reductase, |
| MU5B_HUMAN | Mucin 5B precursor; |
| MY1C_HUMAN | Myosin Ic (Myosin |
| MY1F_HUMAN | Myosin If; Myosin-IE; |
| MYG_HUMAN | Myoglobin. NO INFO |
| MYH2_HUMAN | Myosin heavy chain, |
| MYH7_HUMAN | Myosin heavy chain, |
| MYHB_HUMAN | Myosin heavy chain, |
| MYL4_HUMAN | Myosin light polypeptide |
| MYO6_HUMAN | Myosin VI. NO |
| MYPC_HUMAN | Myosin-binding protein C, |
| N214_HUMAN | Nuclear pore complex |
| NCB1_HUMAN | Nucleobindin 1 precursor |
| NDR3_HUMAN | NDRG3 protein; C: cytoplasm |
| NEB1_HUMAN | Neurabin-I (Neural tissue-specific |
| NEBL_HUMAN | Nebulette (Actin-binding Z-disk |
| NEST_HUMAN | Nestin; C: intermediate filament |
| NGF_HUMAN | Beta-nerve growth factor |
| NHR2_HUMAN | Na(+)/H(+) exchange regulatory |
| NIBL_HUMAN | Niban-like protein NO |
| NIN_HUMAN | Ninein (hNinein) Component |
| NMZ1_HUMAN | Glutamate [NMDA] receptor |
| NNP1_HUMAN | NNP-1 protein; Novel |
| NOL3_HUMAN | Nucleolar protein 3; |
| NP14_HUMAN | Nucleolar phosphoprotein p130 |
| NUKS_HUMAN | Nuclear ubiquitous casein |
| NX1A_HUMAN | Neurexin 1-alpha precursor |
| O00114 | Hypothetical human serine-threonine |
| O00145 | SH2 containing inositol-5-phosphatase; |
| O14827 | Ras-GRF2; F: guanyl-nucleotide exchange |
| O14964 | hypothetical protein P1408 |
| O15059 | KIAA0351 protein; F: guanyl-nucleotide |
| O43302 | KIAA0418 protein NO |
| O60293 | KIAA0546 protein; C: intracellular |
| O60316 | KIAA0570 protein; F: cysteine-type |
| O60466 | TGF beta receptor |
| O60526 | so09f03.y1 Gm-c1035 Glycine |
| O60831 | JM4 [*Homo sapiens*] |
| O75058 | KIAA0470 protein NO |
| O75061 | KIAA0473 protein; F: phosphoprotein |
| O75112 | KIAA0613 protein; F: protein |
| O75815 | Breast cancer antiestrogen |
| O75921 | RNA polymerase II |
| O76045 | Pro alpha 1(I) |
| O95035 | WUGSC: H_RG054D04 NO INFO |
| O96028 | Putative WHSC1 protein; |
| ORP2_HUMAN | Oxysterol binding protein-related |
| OSB1_HUMAN | Oxysterol-binding protein 1; |
| OST4_HUMAN | Dolichyl-diphosphooligosaccharide--protein glycosyltransferaseType I |
| OSTP_HUMAN | Osteopontin precursor; Bone |
| OTOF_HUMAN | Otoferlin (Fer-1 like |
| P2X2_HUMAN | P2X purinoceptor 2; |
| P4H1_HUMAN | Prolyl 4-hydroxylase alpha-1 |
| P5CS_HUMAN | Delta 1-pyrroline-5-carboxylate synthetase; |
| PAPA_HUMAN | Pregnancy-associated plasma protein-A |
| PARA_HUMAN | Alpha-parvin (Calponin-like integrin-linked |
| PCD5_HUMAN | Programmed cell death |
| PCFB_HUMAN | Pre-mRNA cleavage complex |
| PCS1_HUMAN | Phosphofurin acidic cluster |
| PCTL_HUMAN | PCTP-like protein; PCTP-L; |
| PDK3_HUMAN | [Pyruvate dehydrogenase [lipoamide]] |
| PEC1_HUMAN | Platelet endothelial cell |
| PFD2_HUMAN | Prefoldin subunit 2 |
| PFD4_HUMAN | Prefoldin subunit 4 |
| PGBM_HUMAN | Basement membrane-specific heparan |
| PGS1_HUMAN | Biglycan precursor Secreted; |

TABLE 4-continued

Proteins unique to CAP

| Protein ID | Common Name |
| --- | --- |
| PHYI_HUMAN | Phytanoyl-CoA hydroxylase interacting |
| PKC1_HUMAN | Pleckstrin homology domain |
| PKL2_HUMAN | Protein kinase C-like |
| PKP4_HUMAN | Plakophilin 4; p0071; |
| PLO1_HUMAN | Procollagen-lysine, 2-oxoglutarate 5-dioxygenase 1 |
| PLO2_HUMAN | Procollagen-lysine, 2-oxoglutarate 5-dioxygenase 2 |
| PLO3_HUMAN | Procollagen-lysine, 2-oxoglutarate 5-dioxygenase 3 |
| POP1_HUMAN | Ribonucleases P/MRP protein |
| POSN_HUMAN | Periostin precursor; PN; |
| PP1A_HUMAN | Serine/threonine protein phosphatase |
| PPCM_HUMAN | Phosphoenolpyruvate carboxykinase, mitochondrial |
| PRLP_HUMAN | Prolargin precursor Secreted; |
| PSF1_HUMAN | Proteasome inhibitor PI31 |
| Q01720 | FILAGGRIN precursor; PROFILAGGRIN; |
| Q12869 | R kappa B; |
| Q15042 | KIAA0066 protein NO |
| Q15468 | SIL protein; P: cell |
| Q16630 | HPBRII-4 mRNA; HPBRII-7 |
| Q66YK6 | Rap1 interacting factor |
| Q68DE1 | Hypothetical protein DKFZp781J2344 |
| Q68DL8 | Hypothetical protein DKFZp781L0319 |
| Q69YJ2 | Hypothetical protein DKFZp762I0611 |
| Q6AI58 | Hypothetical protein DKFZp781A0295 |
| Q6AW92 | Hypothetical protein DKFZp686C18106 |
| Q6B0H9 | Hypothetical protein NO |
| Q6DJT3 | Organic cation transporter |
| Q6DV90 | Sarcomeric tropomyosin kappa |
| Q6IA00 | FLJ22386 protein NO |
| Q6IBS0 | PTK9L protein; C: intracellular |
| Q6NSI3 | Hypothetical protein NO |
| Q6NUN7 | Hypothetical protein FLJ23554 |
| Q6ZMN5 | Hypothetical protein FLJ16798; |
| Q6ZN20 | Hypothetical protein FLJ16514; |
| Q6ZND8 | Hypothetical protein FLJ16191; |
| Q6ZRT4 | Hypothetical protein FLJ46118 |
| Q6ZSQ4 | Hypothetical protein FLJ45296 |
| Q6ZTW2 | Hypothetical protein FLJ44179 |
| Q6ZV48 | Hypothetical protein FLJ42992 |
| Q7Z2Z4 | Hypothetical protein DKFZp686I14200; |
| Q85KX8 | Cytochrome oxidase subunit |
| Q86VN1 | CGI-145 protein; OTTHUMP00000040889 |
| Q86XD6 | Hypothetical protein FLJ20294 |
| Q8IUI5 | Similar to butyrate-induced |
| Q8IV38 | Ankyrin repeat and |
| Q8IVE9 | KIAA2022 protein NO |
| Q8IWE2 | Hypothetical protein LOC92689 |
| Q8IXW0 | Hypothetical protein MGC35138; |
| Q8IYY4 | Hypothetical protein FLJ32844; |
| Q8IZ53 | C9orf75 protein NO |
| Q8IZ83 | Hypothetical protein MGC10204; |
| Q8N1L6 | Hypothetical protein FLJ40049 |
| Q8N1N4 | Hypothetical protein FLJ39100; |
| Q8N274 | Hypothetical protein FLJ33834 |
| Q8N279 | Hypothetical protein FLJ33811; |
| Q8N3H7 | Hypothetical protein DKFZp761G0314 |
| Q8N3X4 | FLJ20433 protein NO |
| Q8N5G2 | novel protein [Danio |
| Q8N5G8 | LOC157378 protein NO |
| Q8N608 | Dipeptidylpeptidase 10; C: membrane |
| Q8N7U5 | Hypothetical protein FLJ40332 |
| Q8NBG8 | Hypothetical protein FLJ33230 |
| Q8NBS8 | Hypothetical protein FLJ90813; |
| Q8ND87 | Hypothetical protein DKFZp434K0835; |
| Q8NDM2 | Hypothetical protein DKFZp727C181 |
| Q8NEY4 | V-ATPase C2 subunit; |
| Q8NEZ3 | WD repeat membrane |
| Q8NHN5 | Obscurin NO INFO |
| Q8TB65 | Cytochrome c oxidase |
| Q8TBP8 | Formyltetrahydrofolate dehydrogenase, isoform |
| Q8TDA3 | Guanine nucleotide exchange |
| Q8TDJ6 | Rabconnectin NO INFO |
| Q8TEC1 | Hypothetical protein FLJ23660; |
| Q8TEP8 | FLJ00145 protein NO |
| Q8WX93 | Myoneurin NO INFO |
| Q8WY20 | novel protein [Homo |
| Q8WZ09 | Hypothetical protein NO |

TABLE 4-continued

Proteins unique to CAP

| Protein ID | Common Name |
| --- | --- |
| Q8WZ35 | Hypothetical protein DKFZp434P194 |
| Q96B95 | KIAA1799 protein; F: calcium |
| Q96BR8 | LEPRE1 protein; F: oxidoreductase |
| Q96C32 | UBC protein NO |
| Q96CG5 | Hypothetical protein NO |
| Q96E61 | Hypothetical protein NO |
| Q96EK7 | Hypothetical protein KIAA1838; |
| Q96FJ2 | Dynein light chain |
| Q96GX4 | MCM10 protein NO |
| Q96HU8 | Di-Ras2; DIRAS family, |
| Q96KX7 | Thymic dendritic cell-derived |
| Q96NM0 | Hypothetical protein FLJ30596 |
| Q96P57 | C6ORF34B NO INFO |
| Q96QF5 | Septin-9; MLL septin-like |
| Q96SK8 | Hypothetical protein FLJ14791; |
| Q96T23 | HBV pX associated |
| Q9BRG1 | Hypothetical protein MGC10540; |
| Q9BSH5 | Haloacid dehalogenase-like hydrolase |
| Q9BVC6 | Hypothetical protein MGC5508 |
| Q9BVZ1 | C2orf33 protein NO |
| Q9GZT6 | novel protein [Danio |
| Q9H009 | novel protein similar |
| Q9H2F7 | CTCL tumor antigen |
| Q9H6E3 | Hypothetical protein FLJ22351; |
| Q9H7C9 | Hypothetical protein FLJ21035; |
| Q9H8C8 | Hypothetical protein FLJ13755 |
| Q9HCM2 | KIAA1550 protein; C: membrane |
| Q9HD27 | Angiomotin; Hypothetical protein |
| Q9NPR9 | Hypothetical protein; C: integral |
| Q9P273 | KIAA1455 protein NO |
| Q9UDX0 | Oxoglutarate (Alpha-ketoglutarate) dehydrogenase |
| Q9UHV1 | PRO1386 NO INFO |
| Q9UPN4 | KIAA1118 protein; C: muscle |
| Q9UPV4 | KIAA1048 protein; F: ATP |
| Q9Y5Y9 | Sodium channel protein |
| Q9Y662 | Heparan sulfate D-glucosaminyl |
| R27B_HUMAN | Ras-related protein Rab-27B; |
| RAC3_HUMAN | Ras-related C3 botulinum |
| RB31_HUMAN | Ras-related protein Rab-31; |
| RB35_HUMAN | Ras-related protein Rab-35; |
| RB3B_HUMAN | Ras-related protein Rab-3B |
| RCN1_HUMAN | Reticulocalbin 1 precursor; |
| RDHB_HUMAN | Retinol dehydrogenase 11; |
| RDHD_HUMAN | Retinol dehydrogenase 13 |
| RGE6_HUMAN | Rap guanine nucleotide |
| RGSK_HUMAN | Regulator of G-protein |
| RHG4_HUMAN | Rho-GTPase-activating protein 4 |
| RL2B_HUMAN | 60S ribosomal protein |
| RL35_HUMAN | 60S ribosomal protein |
| RL3_HUMAN | 60S ribosomal protein |
| RLA1_HUMAN | 60S acidic ribosomal |
| RM12_HUMAN | 39S ribosomal protein |
| RN17_HUMAN | RING finger protein |
| RNT1_HUMAN | Regulator of nonsense |
| ROCL_HUMAN | novel protein similar |
| ROG_HUMAN | RNA binding motif |
| RS26_HUMAN | 40S ribosomal protein |
| RS4Y_HUMAN | 40S ribosomal protein |
| RT36_HUMAN | Mitochondrial 28S ribosomal |
| RW1_HUMAN | RW1 protein NO |
| S107_HUMAN | S100 calcium-binding protein |
| S108_HUMAN | Calgranulin A (Migration |
| S109_HUMAN | Calgranulin B (Migration |
| S111_HUMAN | Calgizzarin (S100 calcium-binding |
| S113_HUMAN | S100 calcium-binding protein |
| S142_HUMAN | SEC14-like protein 2; |
| S3B1_HUMAN | Splicing factor 3B |
| S6AH_HUMAN | Orphan sodium- and |
| SACS_HUMAN | Sacsin. NO INFO |
| SAMP_HUMAN | Serum amyloid P-component |
| SCA1_HUMAN | Secretory carrier-associated membrane |
| SCA5_HUMAN | Secretory carrier-associated membrane |
| SEN5_HUMAN | Sentrin-specific protease 5; |
| SETX_HUMAN | Probable helicase senataxin; |
| SFD1_HUMAN | Sec1 family domain |
| SG2_HUMAN | Secretogranin II precursor; |

TABLE 4-continued

Proteins unique to CAP

| Protein ID | Common Name |
|---|---|
| SGTB_HUMAN | Small glutamine-rich tetratricopeptide |
| SHC3_HUMAN | SHC transforming protein |
| SJ2B_HUMAN | Synaptojanin 2 binding |
| SM31_HUMAN | Ubiquitin-like protein SMT3A |
| SMC3_HUMAN | Structural maintenance of |
| SN23_HUMAN | Synaptosomal-associated protein 23; |
| SN29_HUMAN | Synaptosomal-associated protein 29; |
| SNG2_HUMAN | Synaptogyrin 2 INTEGRAL |
| SNXP_HUMAN | Sorting nexin 25; |
| SP20_HUMAN | Spartin; Trans-activated by |
| SRC_HUMAN | Proto-oncogene tyrosine-protein kinase |
| SSRA_HUMAN | Translocon-associated protein, alpha |
| STA1_HUMAN | Signal transducer and |
| STAU_HUMAN | Double-stranded RNA-binding protein |
| STOM_HUMAN | Erythrocyte band 7 |
| SX11_HUMAN | Transcription factor SOX-11; |
| SYTC_HUMAN | Synaptotagmin XII Integral |
| SZ11_HUMAN | Small inducible cytokine |
| T2AG_HUMAN | Transcription initiation factor |
| TBCA_HUMAN | Tubulin-specific chaperone A |
| TD53_HUMAN | Tumor protein D53; |
| TES2_HUMAN | Dual specificity testis-specific |
| TF1A_HUMAN | Transcription intermediary factor |
| TF_HUMAN | Tissue factor precursor; |
| TGR3_HUMAN | TGF-beta receptor type |
| THA2_HUMAN | THAP domain protein |
| THA_HUMAN | Thyroid hormone receptor |
| TPCC_HUMAN | Troponin C, slow |
| TRFM_HUMAN | Melanotransferrin precursor Attached |
| TRIC_HUMAN | Troponin I, cardiac |
| TRT2_HUMAN | Troponin T, cardiac |
| TRY1_HUMAN | Trypsin I precursor; |
| TSP1_HUMAN | Thrombospondin 1 precursor |
| TTC1_HUMAN | Tetratricopeptide repeat protein |
| TYPH_HUMAN | deoA [Mycobacterium tuberculosis |
| UBQ2_HUMAN | Ubiquilin 2; Protein |
| UDP2_HUMAN | UTP--glucose-1-phosphate uridylyltransferase 2; |
| URP1_HUMAN | Unc-112 related protein |
| VAG1_HUMAN | Vacuolar ATP synthase |
| VAG2_HUMAN | Vacuolar ATP synthase |
| VAS1_HUMAN | Vacuolar ATP synthase |
| VEGP_HUMAN | Von Ebner's gland |
| VEZA_HUMAN | Vezatin Type III |
| VP36_HUMAN | Vesicular integral-membrane protein |
| VP41_HUMAN | Vacuolar assembly protein |
| VTNC_HUMAN | Vitronectin precursor; Serum |
| WD37_HUMAN | WD-repeat protein 37 |
| WN3A_HUMAN | Wnt-3a protein precursor |
| WWP2_HUMAN | Nedd-4-like E3 ubiquitin-protein |

TABLE 5

Proteins unique to CP

| Protein ID | Common Name |
|---|---|
| 1A01_HUMAN | HLA class I histocompatibility antigen, |
| AASS_HUMAN | Alpha-aminoadipic semialdehyde synthase |
| ABL1_HUMAN | Proto-oncogene tyrosine-protein kinase ABL1; p150; |
| ACN1_HUMAN | Astrotactin 1; P: cell migration NO |
| ACY1_HUMAN | Aminoacylase-1; N-acyl-L-amino-acid amidohydrolase |
| ADAS_HUMAN | Alkyldihydroxyacetonephosphate synthase |
| ADHX_HUMAN | Alcohol dehydrogenase class III chi |
| AIP_HUMAN | AH receptor-interacting protein Cytoplasmic. MAY |
| APL2_HUMAN | Apolipoprotein L2 Cytoplasmic (Probable). May |
| ARH7_HUMAN | Rho guanine nucleotide exchange factor |
| ASML_HUMAN | N-acetylserotonin O-methyltransferase-like protein; ASMTL; F: |
| ATM_HUMAN | Serine-protein kinase ATM PRIMARILY NUCLEAR. |
| ATPJ_HUMAN | ATP synthase e chain, mitochondrial |
| BCS1_HUMAN | Mitochondrial chaperone BCS1; BCS1-like protein; |
| BLMH_HUMAN | Bleomycin hydrolase |
| CA00_HUMAN | Protein CGI-100 precursor; UNQ397/PRO733 |
| CA16_HUMAN | Collagen alpha 1 |

TABLE 5-continued

Proteins unique to CP

| Protein ID | Common Name |
|---|---|
| CA24_HUMAN | Collagen alpha 2 |
| CADA_HUMAN | Cadherin-10 precursor; T2-cadherin; C: integral to |
| CALI_HUMAN | Calicin; C: cytoskeleton Calyx; sperm head |
| CCD6_HUMAN | Coiled-coil domain containing protein 6; |
| CE29_HUMAN | Centrosomal protein Cep290 |
| CEP2_HUMAN | Centrosomal protein 2 |
| CES6_HUMAN | Cat eye syndrome critical region |
| CLI5_HUMAN | Chloride intracellular channel protein 5; |
| CLS1_HUMAN | Calsyntenin-1 precursor Type I membrane |
| CN39_HUMAN | Hypothetical protein C14orf39 |
| COLI_HUMAN | Corticotropin-lipotropin precursor ACTH |
| CPSM_HUMAN | Carbamoyl-phosphate synthase [ammonia] |
| CSN5_HUMAN | COP9 signalosome complex subunit 5; |
| CTD1_HUMAN | Catenin delta-1 Cytoplasmic and nuclear |
| CUT2_HUMAN | Homeobox protein Cux-2; Cut-like 2; |
| CXAR_HUMAN | Coxsackievirus and adenovirus receptor precursor |
| CYA8_HUMAN | Adenylate cyclase, type VIII Integral |
| D3D2_HUMAN | 3,2-trans-enoyl-CoA isomerase, mitochondrial precursor |
| DD37_HUMAN | Probable ATP-dependent helicase DHX37; DEAH-box |
| DJBB_HUMAN | DnaJ homolog subfamily B member |
| DLP1_HUMAN | Disks large-associated protein 1 Membrane-associated |
| DMD_HUMAN | Dystrophin. May play |
| DOC4_HUMAN | Dedicator of cytokinesis protein 4 |
| E15R_HUMAN | Epidermal growth factor receptor substrate |
| ECH1_HUMAN | Delta3,5-delta2,4-dienoyl-CoA isomerase |
| EHD2_HUMAN | EH-domain containing protein 2 NO |
| EMD_HUMAN | Emerin; C: nuclear membrane Nuclear transmembrane |
| ERC1_HUMAN | ERC protein 1 (ELKS protein) |
| ERG7_HUMAN | Lanosterol synthase; Oxidosqualene--lanosterol cyclase; 2,3-e |
| F262_HUMAN | 6-phosphofructo-2-kinase/fructose-2,6-biphosphatase 2 |
| F263_HUMAN | 6-phosphofructo-2-kinase/fructose-2,6-biphosphatase 3 |
| FKB5_HUMAN | FK506-binding protein 5 Nuclear and |
| FYN_HUMAN | Proto-oncogene tyrosine-protein kinase FYN; P59-FYN; |
| G6PE_HUMAN | GDH/6PGL endoplasmic bifunctional protein precursor |
| GAL1_HUMAN | Galactokinase; Galactose kinase; C: cytoplasm NO |
| GBAP_HUMAN | Gamma-aminobutyric acid receptor associated protein; |
| GBG4_HUMAN | Guanine nucleotide-binding protein G NO |
| GBG7_HUMAN | Guanine nucleotide-binding protein G NO |
| GGA1_HUMAN | ADP-ribosylation factor binding protein GGA1; |
| HPCA_HUMAN | Neuron specific calcium-binding protein hippocalcin; |
| HRG_HUMAN | Histidine-rich glycoprotein precursor Secreted. The |
| HS76_HUMAN | Heat shock 70 kDa protein |
| IDI1_HUMAN | Isopentenyl-diphosphate delta-isomerase 1 Peroxisomal. |
| IF5_HUMAN | Eukaryotic translation initiation factor 5 |
| IGB1_HUMAN | Immunoglobulin-binding protein 1; CD79a-binding protein |
| ITA6_HUMAN | Integrin alpha-6 precursor Type I |
| JJ2C_HUMAN | Jumonji domain containing protein 2C; |
| K513_HUMAN | Protein KIAA0513 |
| KHL6_HUMAN | Kelch-like protein 6 |
| KPT3_HUMAN | Serine/threonine-protein kinase PCTAIRE-3; PCTAIRE-motif p |
| LAP4_HUMAN | LAP4 protein; Scribble homolog protein; |
| LCF1_HUMAN | Long-chain-fatty-acid--CoA ligase 1; Long-chain acyl-CoA |
| LMB2_HUMAN | Laminin beta-2 chain precursor Extracellular. |
| LMG1_HUMAN | Laminin gamma-1 chain precursor Extracellular. |
| LPB1_HUMAN | Liprin-beta 1; Protein tyrosine phosphatase |
| LU_HUMAN | Lutheran blood group glycoprotein precursor |
| MAGM_HUMAN | Mitochondria-associated granulocyte macrophage |
| MEC2_HUMAN | Methyl-CpG-binding protein 2; MeCP-2 protein; |
| MPPB_HUMAN | Mitochondrial processing peptidase beta subunit, |
| MY9B_HUMAN | Myosin IXb; Unconventional myosin-9b; C: actin |
| NB7M_HUMAN | NADH-ubiquinone oxidoreductase B17 |
| NCR2_HUMAN | Nuclear receptor co-repressor 2 Nuclear. |
| NGAP_HUMAN | Ras GTPase-activating protein nGAP; RAS |
| NIAM_HUMAN | NADH-ubiquinone oxidoreductase ASHI subunit, |
| NID2_HUMAN | Nidogen-2 precursor Secreted; extracellular matCell |
| NIPM_HUMAN | NADH-ubiquinone oxidoreductase 15 kDa subunit |
| NR54_HUMAN | Non-POU domain-containing octamer-binding protein |
| NU14_HUMAN | Uridine diphosphate glucose pyrophosphatase; |
| NUMA_HUMAN | Nuclear mitotic apparatus protein 1; |
| O14979 | JKTBP2; Heterogeneous nuclear ribonucleoprotein D-like; |
| O43273 | P53 binding protein |
| O43290 | SART-1; Squamous cell carcinoma antigen |
| O60280 | KIAA0528 protein; C: membrane |
| O60735 | dJ69B10.1 (GA17 protein) [Homo sapiens] |
| O75179 | KIAA0697 protein; F: ATP binding |
| O75339 | Cartilage intermediate layer protein; F: phosphoprotein |

TABLE 5-continued

Proteins unique to CP

| Protein ID | Common Name |
| --- | --- |
| O75500 | tad99c12.y1 Hydra EST Darmstadt I |
| O95714 | HERC2 protein; F: guanyl-nucleotide exchange factor |
| O95810 | Serum deprivation response; F: phospholipid binding |
| ODBA_HUMAN | 2-oxoisovalerate dehydrogenase alpha subunit |
| P11A_HUMAN | Phosphatidylinositol-4,5-bisphosphate 3-kinase catalytic subunit |
| P285_HUMAN | Peroxisomal proliferator-activated receptor A interacting |
| P2CA_HUMAN | Protein phosphatase 2C alpha isoform |
| P2G4_HUMAN | Proliferation-associated protein 2G4 |
| PAC2_HUMAN | Protein kinase C and casein |
| PASK_HUMAN | PAS domain containing serine/threonine-protein kinase; |
| PCH7_HUMAN | Protocadherin 7 precursor; Brain-heart protocadherin; |
| PE5R_HUMAN | PEX5-related protein; Peroxin 5-related protein; |
| PHR1_HUMAN | Phosphatase and actin regulator 1 |
| PMVK_HUMAN | Phosphomevalonate kinase; PMKase; C: peroxisome Peroxisomal |
| PSB3_HUMAN | Proteasome subunit beta type 3; |
| PSB5_HUMAN | Proteasome subunit beta type 5 |
| PSD1_HUMAN | 26S proteasome non-ATPase regulatory subunit |
| PSD6_HUMAN | 26S proteasome non-ATPase regulatory subunit |
| PXF_HUMAN | Peroxisomal farnesylated protein PEROXISOMAL |
| Q07666 | P62; KH domain containing, RNA |
| Q13446 | P60; C: cytosol(ISS); F: protein kinase binding |
| Q15598 | Titin; F: structural constituent of muscle |
| Q16219 | Insulin activator factor; C: insulin control |
| Q68CR3 | Hypothetical protein DKFZp781E17107 |
| Q68DL4 | Hypothetical protein DKFZp781J211 |
| Q6BCY4 | Cytochrome b5 reductase b5R NO |
| Q6MZY9 | Hypothetical protein DKFZp686M14237 |
| Q6N046 | Hypothetical protein DKFZp686H15136 |
| Q6NZI2 | Polymerase I and transcript release |
| Q6P5T6 | Hypothetical protein; F: sugar binding NO |
| Q6PRD1 | GPR158-like 1 receptor; C: membrane NO |
| Q6R7N2 | Hemoglobin beta; C: hemoglobin complex NO |
| Q6U7G8 | GTP-GDP dissociation stimulator 1 isoform |
| Q6UX81 | CLCA4; Chloride channel, calcium activated, |
| Q6XYE4 | FP17425 |
| Q6ZML6 | FLJ00267 protein |
| Q6ZRE2 | Hypothetical protein FLJ46424 |
| Q6ZUV0 | Hypothetical protein FLJ43309; F: hydrolase activity |
| Q7Z2K9* | *homo sapiens* (human). dj467I1.1 (kiaa0833) |
| Q86T29 | Hypothetical protein DKFZp686B222; C: nucleus |
| Q86UF3 | Hypothetical protein MGC43026 |
| Q86UQ4 | ABC A13; F: ATP binding |
| Q8IVL1 | steerin2 protein [*Homo sapiens*] |
| Q8IWY7 | novel protein similar to vertebrate |
| Q8IY03 | C9orf77 protein; F: catalytic activity |
| Q8IYE5 | DHX36 protein; F: ATP binding; |
| Q8IYI6 | Exocyst complex 84-kDa subunit; OTTHUMP00000060156 |
| Q8IYS0 | DKFZp434C0328 protein |
| Q8IYU5 | SLCO6A1 protein; C: membrane |
| Q8IYZ3 | EFHA2 protein; F: calcium ion binding |
| Q8IZ16 | Hypothetical gene supported by BC031966 |
| Q8IZP7 | Heparan sulfate 6-O-sulfotransferase 3; F: transferase |
| Q8IZQ1 | ALFY; F: zinc ion binding |
| Q8MML2 | SYNAPTIC DYNAMIN-ASSOCIATED PROTEIN IIBB |
| Q8N264 | Hypothetical protein FLJ33877 |
| Q8N2F4 | Hypothetical protein PSEC0200 |
| Q8N5C0 | BAIAP2 protein Secreted |
| Q8N5E8 | PP3856 protein; F: nicotinate phosphoribosyltransferase activity |
| Q8N5H7 | SH2 domain containing 3C; F: guanyl-nucleotide |
| Q8N6D9 | STAM protein; P: intracellular protein transport |
| Q8N7G2 | Hypothetical protein FLJ25675 |
| Q8N883 | Hypothetical protein FLJ39837 |
| Q8N8N7 | Hypothetical protein FLJ39091; Zinc binding |
| Q8N987 | Hypothetical protein FLJ38214; Neuronal calcium |
| Q8N9P3 | Hypothetical protein FLJ36794 |
| Q8NCZ9 | Hypothetical protein DKFZp566B1447 |
| Q8NHP6 | Motile sperm domain containing 2; |
| Q8TDR0 | Interleukin 13 receptor alpha 1-binding |
| Q8TED6 | Hypothetical protein FLJ23617; F: hydrolase activity |
| Q8WXE8 | Paraspeckle protein 1 beta isoform |
| Q969L9 | RNA binding protein HQK; RNA |
| Q96A33 | Hypothetical protein FLJ14938; Hypothetical protein |
| Q96B17 | Hypothetical protein; F: protein binding |
| Q96CH9 | Hypothetical protein KIAA1244 |
| Q96EI3 | PTD012 protein |
| Q96GA9 | V-crk sarcoma virus CT10 oncogene |

TABLE 5-continued

| Proteins unique to CP | |
|---|---|
| Protein ID | Common Name |
| Q96H23 | FLJ10579 protein |
| Q96JJ7 | KIAA1830 protein; F: calcium ion binding |
| Q96JN2 | KIAA1793 protein |
| Q96LU3 | Hypothetical protein FLJ25064 |
| Q96MG1 | Hypothetical protein FLJ32421 |
| Q96S83 | Hypothetical protein |
| Q99442 | Translocation protein-1; TLOC1 protein; Sec62; |
| Q9BRA2 | Hypothetical protein TXNL5; Putative 42-9-9 |
| Q9BRF8 | Hypothetical protein FLJ11151; CSTP1; F: hydrolase |
| Q9C0B1 | KIAA1752 protein |
| Q9GZT3 | DC50; DC23; Hypothetical protein PD04872; |
| Q9HAJ2 | Hypothetical protein FLJ11539 |
| Q9NQ48 | Leucine zipper transcription factor-like 1; |
| Q9NY47 | Calcium channel, alpha 2/delta subunit |
| Q9UD80 | Neuronal voltage-dependent calcium channel alpha |
| Q9ULH4 | KIAA1246 protein |
| Q9ULM3 | KIAA1197 protein |
| Q9UNU8 | Hypothetical protein; C |
| Q9Y485 | X-like 1 protein; F: protein binding |
| R23A_HUMAN | UV excision repair protein RAD23 |
| RAP1_HUMAN | Rab GTPase binding effector protein |
| RFL1_HUMAN | Ret finger protein-like 1; RING |
| RGP1_HUMAN | Ran GTPase-activating protein 1 |
| RGP2_HUMAN | Rap1 GTPase-activating protein 1; Rap1GAP; |
| RGSC_HUMAN | Regulator of G-protein signaling 12 |
| RL22_HUMAN | 60S ribosomal protein L22; Epstein-Barr |
| RL31_HUMAN | 60S ribosomal protein L31 |
| ROH1_HUMAN | heterogeneous nuclear ribonucleoprotein H/F, putative |
| ROH2_HUMAN | Heterogeneous nuclear ribonucleoprotein H' Nuclear; |
| RPGR_HUMAN | X-linked retinitis pigmentosa GTPase regulator |
| RUV2_HUMAN | RuvB-like 2 (48-kDa TATA box-binding |
| SC63_HUMAN | Translocation protein SEC63 homolog Integral |
| SCL2_HUMAN | Sex comb on midleg-like protein |
| SF45_HUMAN | Splicing factor 45 Nuclear. |
| SGA2_HUMAN | SLIT-ROBO Rho GTPase activating protein |
| SHP1_HUMAN | SH3-domain kinase binding protein 1 |
| SM3A_HUMAN | Semaphorin 3A precursor; Semaphorin III; |
| SMC2_HUMAN | Structural maintenance of chromosome 2-like |
| SNPH_HUMAN | Syntaphilin; F: syntaxin-1 binding Membrane-associated Inhibits |
| SP8_HUMAN | Transcription factor Sp8; Specificity protein |
| SQRD_HUMAN | Sulfide: quinone oxidoreductase, mitochondrial precursor; CGI- |
| SR14_HUMAN | Signal recognition particle 14 kDa |
| SRC8_HUMAN | Src substrate cortactin Cytoplasmic. Associated |
| SUM2_HUMAN | Sulfatase modifying factor 2 precursor; |
| SYT2_HUMAN | Synaptotagmin-2; Synaptotagmin II; SytII Synaptic |
| T103_HUMAN | Tetratricopeptide repeat protein KIAA0103 Nuclear |
| T150_HUMAN | Thyroid hormone receptor-associated protein complex |
| TAC1_HUMAN | Transforming acidic coiled-coil-containing protein 1 |
| TBBQ_HUMAN | Tubulin beta-4q chain |
| TGM1_HUMAN | Protein-glutamine gamma-glutamyltransferase K |
| TIAM_HUMAN | T-lymphoma invasion and metastasis inducing |
| TIE1_HUMAN | Tyrosine-protein kinase receptor Tie-1 precursor |
| TLRA_HUMAN | Toll-like receptor 10 precursor Type |
| TM24_HUMAN | Transmembrane protein 24; DLNB23 protein |
| TMO1_HUMAN | Tropomodulin 1 |
| TRIA_HUMAN | Thyroid receptor interacting protein 11 |
| TXN4_HUMAN | Thioredoxin domain containing protein 4 |
| TXTP_HUMAN | Tricarboxylate transport protein, mitochondrial precursor; |
| U84B_HUMAN | Sad1/unc-84-like protein 2; Rab5 interacting |
| UB37_HUMAN | Ubiquitin carboxyl-terminal hydrolase 37; Ubiquitin |
| UBQ1_HUMAN | Ubiquilin 1; Protein linking IAP |
| UBQ4_HUMAN | Ubiquilin 4; Ataxin-1 ubiquitin-like interacting |
| UN5A_HUMAN | Netrin receptor UNC5A precursor; Unc-5 |
| VATF_HUMAN | Vacuolar ATP synthase subunit F; |
| WAS2_HUMAN | WAS protein family, member 2 |
| Z217_HUMAN | Zinc finger protein 217 Nuclear |
| ZYX_HUMAN | Zyxin (Zyxin 2) |

What is claimed is:

1. A method for treating multiple sclerosis in a patient, the method comprising:

selecting a patient having chronic active plaque (CAP) type lesions wherein the lesion is typed by determining an increase in expression of at least one protein involved in coagulation, selected from the group consisting of tissue factor (TF) and protein C inhibitor (PCI); and administering to said patient a therapeutically effective dose of an activated protein C protein or a fragment thereof for a period of time sufficient to decrease the severity of multiple sclerosis.

2. The method of claim 1, wherein the activated protein C protein is Drotrecogin alpha.

3. The method of claim 1, wherein the activated protein C protein is a variant of activated protein C having reduced anticoagulant activity.

4. The method of claim 1, wherein multiple doses of the activated protein C protein or fragments thereof are administered over a period of time.

* * * * *

SEQUENCE LISTING

<160> NUMBER OF SEQ ID NOS: 4

<210> SEQ ID NO 1
<211> LENGTH: 10
<212> TYPE: PRT
<213> ORGANISM: Homo sapiens

<400> SEQUENCE: 1

```
Asp Leu Ile Tyr Thr Leu Tyr Tyr Trp Lys
 1               5                  10
```

<210> SEQ ID NO 2
<211> LENGTH: 295
<212> TYPE: PRT
<213> ORGANISM: Homo Sapiens

<400> SEQUENCE: 2

```
Met Glu Thr Pro Ala Trp Pro Arg Val Pro Arg Pro Glu Thr Ala Val
 1               5                  10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
 50                  55                  60

Val Tyr Thr Val Gln Ile Ser Thr Lys Ser Gly Asp Trp Lys Ser Lys
 65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
               100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
        290                 295
```

```
<210> SEQ ID NO 3
<211> LENGTH: 11
<212> TYPE: PRT
<213> ORGANISM: Homo sapiens

<400> SEQUENCE: 3

Ala Val Val Glu Val Asp Glu Ser Gly Thr Arg
 1               5                  10

<210> SEQ ID NO 4
<211> LENGTH: 403
<212> TYPE: PRT
<213> ORGANISM: Homo sapiens

<400> SEQUENCE: 4

Met Gln Leu Phe Leu Leu Leu Cys Leu Val Leu Leu Ser Pro Gln Gly
 1               5                  10                  15

Ala Ser Leu His Arg His His Pro Arg Glu Met Lys Lys Arg Val Glu
                20                  25                  30

Asp Leu His Val Gly Ala Thr Val Ala Pro Ser Ser Arg Arg Asp Phe
            35                  40                  45

Thr Phe Asp Leu Tyr Arg Ala Leu Ala Ser Ala Ala Pro Ser Gln Asn
        50                  55                  60

Ile Phe Phe Ser Pro Val Ser Ile Ser Met Ser Leu Ala Met Leu Ser
 65                  70                  75                  80

Leu Gly Ala Gly Ser Ser Thr Lys Met Gln Ile Leu Glu Gly Leu Gly
                85                  90                  95

Leu Asn Leu Gln Lys Ser Ser Glu Lys Glu Leu His Gly Phe Gln Gln
            100                 105                 110

Leu Leu Gln Glu Leu Asn Gln Pro Arg Asp Gly Phe Gln Leu Ser Leu
        115                 120                 125

Gly Asn Ala Leu Phe Thr Asp Leu Val Val Asp Leu Gln Asp Thr Phe
    130                 135                 140

Val Ser Ala Met Lys Thr Leu Tyr Leu Ala Asp Thr Phe Pro Thr Asn
145                 150                 155                 160

Phe Asp Ser Ala Gly Ala Met Lys Gln Ile Asn Asp Tyr Val Ala Lys
                165                 170                 175

Gln Thr Lys Gly Lys Ile Val Asp Leu Leu Lys Asn Leu Asp Ser Asn
            180                 185                 190

Ala Val Val Ile Met Val Asn Tyr Ile Phe Phe Lys Ala Lys Trp Glu
        195                 200                 205

Thr Ser Phe Asn His Lys Gly Thr Gln Glu Gln Asp Phe Tyr Val Thr
    210                 215                 220

Ser Glu Thr Val Val Arg Val Pro Met Met Ser Arg Glu Asp Gln Tyr
225                 230                 235                 240

His Tyr Leu Leu Asp Arg Asn Leu Ser Cys Arg Val Val Gly Val Pro
                245                 250                 255

Tyr Gln Gly Asn Ala Thr Ala Leu Phe Ile Pro Ser Glu Gly Lys Met
            260                 265                 270

Gln Gln Val Glu Asn Gly Leu Ser Glu Lys Thr Leu Arg Lys Trp Leu
        275                 280                 285

Lys Met Phe Lys Lys Arg Gln Leu Glu Leu Tyr Leu Pro Lys Phe Ser
    290                 295                 300

Ile Glu Gly Ser Tyr Gln Leu Glu Lys Val Leu Pro Ser Leu Gly Ile
305                 310                 315                 320

Ser Asn Val Phe Thr Ser His Ala Asp Leu Ser Gly Ile Ser Asn His
```

-continued

```
                         325                     330                     335
    Ser Asn Ile Gln Val Ser Glu Met Val His Lys Ala Val Val Glu Val
                    340                     345                 350

Asp Glu Ser Gly Thr Arg Ala Ala Ala Ala Thr Gly Thr Ile Phe Thr
                355                     360                 365

Phe Arg Ser Ala Arg Leu Asn Ser Gln Arg Leu Val Phe Asn Arg Pro
            370                     375                 380

Phe Leu Met Phe Ile Val Asp Asn Asn Ile Leu Phe Leu Gly Lys Val
    385                     390                     395                 400

Asn Arg Pro
```